United States Patent
Brady et al.

(10) Patent No.: US 9,504,560 B2
(45) Date of Patent: *Nov. 29, 2016

(54) ACCOMMODATING INTRAOCULAR LENS WITH OUTER SUPPORT STRUCTURE

(71) Applicant: Abbott Medical Optics Inc., Santa Ana, CA (US)

(72) Inventors: Daniel G. Brady, San Juan Capistrano, CA (US); Michael D Lowery, Irvine, CA (US); Marlene L Paul, Laguna Niguel, CA (US); Stephen W Laguette, Santa Barbara, CA (US); Robert E Glick, Lake Forest, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,557

(22) Filed: Dec. 21, 2012

(65) Prior Publication Data

US 2014/0012375 A1    Jan. 9, 2014

Related U.S. Application Data

(60) Division of application No. 12/840,843, filed on Jul. 21, 2010, now Pat. No. 8,343,216, which is a continuation of application No. 11/322,068, filed on Dec. 28, 2005, now Pat. No. 7,763,069, which is a
(Continued)

(51) Int. Cl.
    *A61F 2/16*    (2006.01)

(52) U.S. Cl.
    CPC .......... *A61F 2/1624* (2013.01); *A61F 2/1629* (2013.01); *A61F 2/1635* (2013.01); *A61F 2/1648* (2013.01); *A61F 2/1694* (2013.01); *A61F 2002/169* (2015.04); *A61F 2002/1682* (2015.04)

(58) Field of Classification Search
    CPC .. A61F 1/1613; A61F 1/1681; A61F 1/1629; A61F 1/1624; A61F 2/1624; A61F 2002/1682

USPC .......... 623/6.38, 6.4, 6.43, 6.46, 6.47, 6.49, 623/6.51, 6.52, 6.53, 6.54, 6.42
See application file for complete search history.

(56) References Cited

U.S. PATENT DOCUMENTS

| | | | |
|---|---|---|---|
| 1,483,509 | A | 5/1921 | Bugbee |
| 2,129,305 | A | 9/1938 | William |

(Continued)

FOREIGN PATENT DOCUMENTS

| | | |
|---|---|---|
| AU | 3225789 A1 | 10/1989 |
| CH | 681687 A5 | 5/1993 |

(Continued)

OTHER PUBLICATIONS

Amo Specs Model AC-21B, 1992.
(Continued)

*Primary Examiner* — David H Willse
*Assistant Examiner* — Javier Blanco
(74) *Attorney, Agent, or Firm* — Abbott Medical Optics Inc.

(57) ABSTRACT

An intraocular lens for insertion into the capsular bag of an eye contains an optic, an outer periphery, and an outer support structure. The optic has a periphery and centered about an optical axis. The outer periphery is disposed about the optic and configured to engage an equatorial region of the capsular bag of an eye. The outer support structure is disposed along the periphery and spaced from the optic with voids outer support structure and the optic. The intraocular lens further comprises a first intermediate member and a weakened region disposed along the outer periphery between the outer support structure and the first intermediate member. The first intermediate member operably couples the optic and the outer support structure. The weakened region is attached to, and configured to provide relative motion between, the outer support structure and the first intermediate member in response to the ciliary muscle of the eye.

11 Claims, 11 Drawing Sheets

Related U.S. Application Data continuation-in-part of application No. 10/661,410, filed on Sep. 12, 2003, now Pat. No. 7,150,759, which is a continuation-in-part of application No. 10/341,701, filed on Jan. 14, 2003, now Pat. No. 7,025,783.

(60) Provisional application No. 60/348,705, filed on Jan. 14, 2002, provisional application No. 60/372,309, filed on Apr. 12, 2002.

(56) References Cited

U.S. PATENT DOCUMENTS

| | | |
|---|---|---|
| 2,274,142 A | 2/1942 | Houchin |
| 2,405,989 A | 8/1946 | Beach |
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,222,432 A | 12/1965 | Grandperret |
| 3,227,507 A | 1/1966 | William |
| 3,305,294 A | 2/1967 | Alvarez |
| 3,339,997 A | 9/1967 | Wesley |
| 3,415,597 A | 12/1968 | Willard |
| 3,420,006 A | 1/1969 | Howard |
| 3,431,327 A | 3/1969 | George |
| 3,482,906 A | 12/1969 | David |
| 3,507,565 A | 4/1970 | Luis et al. |
| 3,542,461 A | 11/1970 | Louis et al. |
| 3,583,790 A | 6/1971 | Baker |
| 3,617,116 A | 11/1971 | Jones |
| 3,632,696 A | 1/1972 | Jones |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |

(56) References Cited

U.S. PATENT DOCUMENTS

| | | |
|---|---|---|
| 4,693,716 A | 9/1987 | MacKool |
| RE32,525 E | 10/1987 | Pannu |
| 4,702,244 A | 10/1987 | Mazzocco |
| 4,704,016 A | 11/1987 | De Carle |
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,781,718 A | 11/1988 | Lindstrom |
| 4,787,903 A | 11/1988 | Grendahl |
| 4,790,847 A | 12/1988 | Woods |
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |
| 4,828,558 A | 5/1989 | Kelman |
| 4,830,481 A | 5/1989 | Futhey et al. |
| 4,834,749 A | 5/1989 | Orlosky |
| 4,840,627 A | 6/1989 | Blumenthal |
| 4,842,601 A | 6/1989 | Smith |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,080 A | 2/1991 | Shepard |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider et al. |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang et al. |
| RE34,998 E | 7/1995 | Langerman |
| 5,443,506 A | 8/1995 | Garabet |
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |

(56) References Cited

U.S. PATENT DOCUMENTS

| | | |
|---|---|---|
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A | 6/1998 | McDonald |
| 5,770,125 A | 6/1998 | O'Connor et al. |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,139,576 A | 10/2000 | Doyle et al. |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 | 3/2001 | Cumming |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 | 5/2001 | Lang et al. |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 | 9/2002 | Woods |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skotton |
| 6,468,306 B1 | 10/2002 | Paul et al. |
| 6,474,814 B1 | 11/2002 | Griffin |
| 6,475,240 B1 | 11/2002 | Paul |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 | 7/2003 | Weinschenk, III et al. |
| 6,616,691 B1 | 9/2003 | Tran |
| 6,616,692 B1 | 9/2003 | Glick et al. |
| 6,616,693 B1* | 9/2003 | Nguyen ............. 623/6.43 |
| 6,638,305 B2 | 10/2003 | Laguette |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,685,315 B1 | 2/2004 | De Carle |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,827,738 B2 | 12/2004 | Willis et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,262 B2 | 4/2005 | Brady et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |

(56) References Cited

U.S. PATENT DOCUMENTS

| | | |
|---|---|---|
| 6,930,838 B2 | 8/2005 | Schachar |
| 6,932,839 B1 | 8/2005 | Kamerling et al. |
| 6,942,695 B1 | 9/2005 | Chapoy et al. |
| 7,018,409 B2 | 3/2006 | Glick et al. |
| 7,021,760 B2 | 4/2006 | Newman |
| 7,025,783 B2 | 4/2006 | Brady et al. |
| 7,041,134 B2 | 5/2006 | Nguyen et al. |
| 7,073,906 B1 | 7/2006 | Portney |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,150,759 B2 | 12/2006 | Paul et al. |
| 7,179,292 B2 | 2/2007 | Worst et al. |
| 7,182,780 B2 | 2/2007 | Terwee et al. |
| 7,186,266 B2 | 3/2007 | Peyman |
| 7,188,949 B2 | 3/2007 | Bandhauer et al. |
| 7,198,640 B2 | 4/2007 | Nguyen |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,247,168 B2 | 7/2007 | Esch et al. |
| 7,261,737 B2 | 8/2007 | Esch et al. |
| 7,452,362 B2 | 11/2008 | Zadno-Azizi et al. |
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 8,052,752 B2 | 11/2011 | Woods et al. |
| 2001/0001836 A1 | 5/2001 | Cumming |
| 2001/0004708 A1 | 6/2001 | Nagai |
| 2001/0018612 A1 | 8/2001 | Carson et al. |
| 2001/0039451 A1 | 11/2001 | Barnett |
| 2001/0044657 A1 | 11/2001 | Kellan |
| 2002/0004682 A1 | 1/2002 | Zhou et al. |
| 2002/0011167 A1 | 1/2002 | Figov et al. |
| 2002/0072796 A1 | 6/2002 | Hoffmann et al. |
| 2002/0095212 A1 | 7/2002 | Boehm |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116058 A1 | 8/2002 | Zadno-Azizi et al. |
| 2002/0116060 A1 | 8/2002 | Nguyen et al. |
| 2002/0120329 A1 | 8/2002 | Lang et al. |
| 2002/0151973 A1 | 10/2002 | Arita et al. |
| 2002/0161434 A1 | 10/2002 | Laguette et al. |
| 2002/0188351 A1 | 12/2002 | Laguette |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0020425 A1 | 1/2003 | Ricotti |
| 2003/0033013 A1 | 2/2003 | Callahan et al. |
| 2003/0045933 A1* | 3/2003 | Brady ................. 623/6.46 |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0105522 A1 | 6/2003 | Glazier |
| 2003/0109925 A1 | 6/2003 | Ghazizadeh et al. |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1* | 8/2003 | Brady et al. ................. 623/6.37 |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0054408 A1 | 3/2004 | Glick et al. |
| 2004/0082993 A1 | 4/2004 | Woods |
| 2004/0082994 A1 | 4/2004 | Woods et al. |
| 2004/0082995 A1 | 4/2004 | Woods |
| 2004/0106992 A1 | 6/2004 | Lang et al. |
| 2004/0111151 A1 | 6/2004 | Paul et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0162612 A1 | 8/2004 | Portney et al. |
| 2004/0167621 A1 | 8/2004 | Peyman |
| 2004/0181279 A1 | 9/2004 | Nun |
| 2004/0215340 A1 | 10/2004 | Messner et al. |
| 2004/0230299 A1 | 11/2004 | Simpson et al. |
| 2004/0230300 A1 | 11/2004 | Bandhauer et al. |
| 2004/0236422 A1 | 11/2004 | Zhang et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0113914 A1 | 5/2005 | Miller et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0234547 A1 | 10/2005 | Nguyen et al. |
| 2005/0246019 A1 | 11/2005 | Blake et al. |
| 2005/0267575 A1 | 12/2005 | Nguyen et al. |
| 2005/0288785 A1 | 12/2005 | Portney et al. |
| 2006/0030938 A1 | 2/2006 | Altmann |
| 2006/0064162 A1 | 3/2006 | Klima |
| 2006/0095127 A1 | 5/2006 | Feingold et al. |
| 2006/0098162 A1 | 5/2006 | Bandhauer et al. |
| 2006/0100703 A1 | 5/2006 | Evans et al. |
| 2006/0111776 A1 | 5/2006 | Glick et al. |
| 2006/0116764 A1 | 6/2006 | Simpson |
| 2006/0116765 A1 | 6/2006 | Blake et al. |
| 2006/0178741 A1 | 8/2006 | Zadno-Azizi et al. |
| 2006/0184244 A1 | 8/2006 | Nguyen et al. |
| 2006/0209430 A1 | 9/2006 | Spivey |
| 2006/0235513 A1 | 10/2006 | Price, Jr. |
| 2006/0238702 A1 | 10/2006 | Glick et al. |
| 2006/0259139 A1 | 11/2006 | Zadno-Azizi et al. |
| 2006/0271187 A1 | 11/2006 | Zadno-Azizi et al. |
| 2007/0050025 A1 | 3/2007 | Nguyen et al. |
| 2007/0067872 A1 | 3/2007 | Mittendorf et al. |
| 2007/0078515 A1 | 4/2007 | Brady |
| 2007/0088433 A1 | 4/2007 | Esch et al. |
| 2007/0100444 A1 | 5/2007 | Brady et al. |
| 2007/0106381 A1 | 5/2007 | Blake |
| 2007/0108643 A1 | 5/2007 | Zadno-Azizi et al. |
| 2007/0123591 A1 | 5/2007 | Kuppuswamy et al. |
| 2007/0129798 A1 | 6/2007 | Chawdhary |
| 2007/0135915 A1 | 6/2007 | Klima |
| 2007/0213817 A1 | 9/2007 | Esch et al. |

(56) References Cited

U.S. PATENT DOCUMENTS

| | | |
|---|---|---|
| 2007/0260309 A1 | 11/2007 | Richardson |
| 2007/0299487 A1 | 12/2007 | Shadduck |
| 2008/0004699 A1 | 1/2008 | Ben Nun |
| 2008/0046076 A1 | 2/2008 | Rombach |
| 2008/0125790 A1 | 5/2008 | Tsai et al. |
| 2008/0161913 A1 | 7/2008 | Brady et al. |
| 2008/0161914 A1 | 7/2008 | Brady et al. |
| 2009/0012609 A1 | 1/2009 | Geraghty et al. |
| 2010/0057203 A1 | 3/2010 | Glick et al. |

FOREIGN PATENT DOCUMENTS

| | | |
|---|---|---|
| DE | 2702117 A1 | 7/1978 |
| DE | 3246306 A1 | 6/1984 |
| DE | 4038088 A1 | 6/1992 |
| DE | 19501444 A1 | 7/1996 |
| DE | 19951148 A1 | 4/2001 |
| DE | 20109306 U1 | 8/2001 |
| DE | 10059482 A1 | 6/2002 |
| DE | 10125829 A1 | 11/2002 |
| EP | 64812 A2 | 11/1982 |
| EP | 162573 A2 | 11/1985 |
| EP | 212616 A2 | 3/1987 |
| EP | 246216 A2 | 11/1987 |
| EP | 328117 A2 | 8/1989 |
| EP | 329981 A1 | 8/1989 |
| EP | 331457 A2 | 9/1989 |
| EP | 336877 A1 | 10/1989 |
| EP | 0337390 A2 | 10/1989 |
| EP | 0342895 A2 | 11/1989 |
| EP | 351471 A2 | 1/1990 |
| EP | 356050 A1 | 2/1990 |
| EP | 337390 A3 | 5/1990 |
| EP | 402825 A1 | 12/1990 |
| EP | 420549 A2 | 4/1991 |
| EP | 470811 A2 | 2/1992 |
| EP | 478929 A1 | 4/1992 |
| EP | 480748 A1 | 4/1992 |
| EP | 488835 A1 | 6/1992 |
| EP | 492126 A2 | 7/1992 |
| EP | 507292 A1 | 10/1992 |
| EP | 566170 A1 | 10/1993 |
| EP | 601845 A1 | 6/1994 |
| EP | 605841 A1 | 7/1994 |
| EP | 691109 A1 | 1/1996 |
| EP | 766540 A1 | 4/1997 |
| EP | 779063 A1 | 6/1997 |
| EP | 780718 A1 | 6/1997 |
| EP | 897702 A2 | 2/1999 |
| EP | 766540 B1 | 8/1999 |
| EP | 1108402 A2 | 6/2001 |
| EP | 1321112 A1 | 6/2003 |
| EP | 1647241 A2 | 4/2006 |
| EP | 1424049 B1 | 6/2009 |
| FR | 488835 A | 11/1918 |
| FR | 2666504 A1 | 3/1992 |
| FR | 2666735 A1 | 3/1992 |
| FR | 2681524 A1 | 3/1993 |
| FR | 2745711 A1 | 9/1997 |
| FR | 2778093 A1 | 11/1999 |
| FR | 2784575 A1 | 4/2000 |
| GB | 939016 A | 10/1963 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| JP | 0211134 | 1/1990 |
| JP | 2126847 A | 5/1990 |
| JP | H06508279 | 9/1994 |
| JP | 7005399 A2 | 1/1995 |
| JP | 7222760 A2 | 8/1995 |
| JP | 9501856 T2 | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | 8404449 A1 | 11/1984 |
| WO | 8603961 A1 | 7/1986 |
| WO | 8700299 A1 | 1/1987 |
| WO | 8707496 A1 | 12/1987 |
| WO | 8803961 A1 | 6/1988 |
| WO | 8902251 A1 | 3/1989 |
| WO | 8911672 A1 | 11/1989 |
| WO | 8911872 A1 | 12/1989 |
| WO | 9000889 A1 | 2/1990 |
| WO | 9109336 A1 | 6/1991 |
| WO | 9302639 A1 | 2/1993 |
| WO | 9305733 A1 | 4/1993 |
| WO | 9416648 A1 | 8/1994 |
| WO | 9503783 A1 | 2/1995 |
| WO | 9610968 A1 | 4/1996 |
| WO | 9615734 A2 | 5/1996 |
| WO | 9625126 A1 | 8/1996 |
| WO | 9635398 A1 | 11/1996 |
| WO | 9712272 A1 | 4/1997 |
| WO | 9727825 A1 | 8/1997 |
| WO | 9743984 A1 | 11/1997 |
| WO | 9805273 A1 | 2/1998 |
| WO | 9821621 A1 | 5/1998 |
| WO | 9849594 A1 | 11/1998 |
| WO | 9856315 A1 | 12/1998 |
| WO | 9903427 A1 | 1/1999 |
| WO | 9907309 A1 | 2/1999 |
| WO | 9920206 A1 | 4/1999 |
| WO | 9921491 A1 | 5/1999 |
| WO | 9929266 A1 | 6/1999 |
| WO | 0021467 A1 | 4/2000 |
| WO | 0027315 A1 | 5/2000 |
| WO | 0035379 A1 | 6/2000 |
| WO | 0046629 A1 | 8/2000 |
| WO | 0059407 A1 | 10/2000 |
| WO | 0061036 A1 | 10/2000 |
| WO | 0066037 A1 | 11/2000 |
| WO | 0066039 A1 | 11/2000 |
| WO | 0066040 A1 | 11/2000 |
| WO | 0066041 A1 | 11/2000 |
| WO | 0108605 A1 | 2/2001 |
| WO | 0119288 A1 | 3/2001 |
| WO | 0119289 A1 | 3/2001 |
| WO | 0128144 A1 | 4/2001 |
| WO | 0134061 A1 | 5/2001 |
| WO | 0134066 A1 | 5/2001 |
| WO | 0134067 A1 | 5/2001 |
| WO | 0156510 A1 | 8/2001 |
| WO | 0160286 A1 | 8/2001 |
| WO | 0164135 A1 | 9/2001 |
| WO | 0164136 A2 | 9/2001 |
| WO | 0166042 A1 | 9/2001 |
| WO | 0182839 A1 | 11/2001 |
| WO | 0189816 A1 | 11/2001 |
| WO | 0209620 A1 | 2/2002 |
| WO | 0212523 A2 | 2/2002 |
| WO | 0219949 A2 | 3/2002 |
| WO | 02058391 A2 | 7/2002 |
| WO | 02071983 A1 | 9/2002 |
| WO | 02098328 A1 | 12/2002 |
| WO | 03009051 A2 | 1/2003 |
| WO | 03015657 A2 | 2/2003 |
| WO | 03015669 A1 | 2/2003 |
| WO | 03034949 A2 | 5/2003 |
| WO | 03049646 A2 | 6/2003 |
| WO | 03057081 A2 | 7/2003 |
| WO | 03059196 A2 | 7/2003 |
| WO | 03059208 A2 | 7/2003 |
| WO | 03075810 A1 | 9/2003 |

(56) References Cited

FOREIGN PATENT DOCUMENTS

| | | |
|---|---|---|
| WO | 03084441 A1 | 10/2003 |
| WO | 03092552 A1 | 11/2003 |
| WO | 04000171 A1 | 12/2003 |
| WO | 2004020549 A1 | 3/2004 |
| WO | 2004037127 A2 | 5/2004 |
| WO | 2004073559 A1 | 9/2004 |
| WO | 2005011531 A2 | 2/2005 |
| WO | 2005018504 A1 | 3/2005 |
| WO | 2005019871 A2 | 3/2005 |
| WO | 03082147 A3 | 8/2005 |
| WO | 2005084587 A2 | 9/2005 |
| WO | 2005115278 A1 | 12/2005 |
| WO | 2006025726 A1 | 3/2006 |
| WO | 2006118452 A1 | 11/2006 |
| WO | 2007040964 A1 | 4/2007 |
| WO | 2007067872 A2 | 6/2007 |
| WO | 2008077795 A2 | 7/2008 |
| WO | 2008079671 A1 | 7/2008 |
| ZA | 0888414 | 11/1988 |

OTHER PUBLICATIONS

Chiron Vision, Nuvita Mar. 20, 1997 (Chiron Vision Corp. 1997), 6 pages.
DVD New Elliptical Accommodating IOL for Cataract Surgery shown at ASCRS Symposium on Apr. 1, 1999.
"DVD titled "New elliptical accommodative IOL for cataract surgery" shown at ASCRS Symposium on Apr. 10, 1999."
English translation of WO93/05733A1.
Fechner P.U., et al., "Iris-Claw Lens in Phakic Eyes to Correct Hyperopia: Preliminary Study," Journal of Cataract and Refractive Surgery , 1998, vol. 24 (1), pp. 48-56.
Hara T., et al., "Accommodative Intraocular Lens with Spring Action Part 1 Design and Placement in an Excised Animal Eye," Ophthalmic Surgery, 1990, vol. 21 (2), pp. 128-133.
International Preliminary Report on Patentability and Written Opinion for Application No. PCT/US2004/29704, mailed on Mar. 13, 2006, 8 pages.
International Preliminary Report on Patentability and Written Opinion for Application No. PCT/US2006/61671, mailed on Jul. 1, 2008, 7 pages.
International Search Report for Application No. PCT/US2003/01270, mailed on Jun. 25, 2003, 5 pages.
International Search Report for Application No. PCT/US2004/29704, mailed on Jan. 25, 2005, 3 pages.
International Search Report for Application No. PCT/US2006/61671, mailed on Apr. 5, 2007, 3 pages.
Mandell R.B. "Contact Lens Practice", 4th Edition, Charles C. Thomas Publishers.
Mandell R.B., et al., "Mathematical Model of the Corneal Contour," School of Optometry, University of California, Berkeley, pp. 183-197.
Menezo J.L., et al., "Endothelial Study of Iris-Claw Phakic Lens: Four Year Follow-Up," Journal of Cataract Refractive Surgery, 1998, vol. 24 (8), pp. 1039-1049.
Office Action mailed Jul. 19, 2011 for Japanese Application No. 2006526344 filed Sep. 10, 2004.
Partial Program Re: ASCRS Symposium, Showing Video Tape Shown Between Apr. 10-14, 1999.
"Program from ASCRS Symposium showing video tape between Apr. 10-14, 1999, 2 pages."
Simonov A.N., et al., "Cubic Optical Elements for an Accommodative Intraocular Lens," Optics Express, 2006, vol. 14 (17), pp. 7757-7775.
Study Design of Nuvita, Mar. 20, 1997, 5 pages.
Thornton S., "Accommodation in Pseudophakia," 1991, pp. 159-162.
U.S. Appl. No. 10/280,918, filed Aug. 5, 2003.

U.S. Appl. No. 10/280,937, filed Oct. 25, 2005.
Adler-Grinberg D., "Questioning Our Classical Understanding of Accommodation and Presbyopia," American Journal of Optometry & Physiological Optics, 1986, vol. 63 (7), pp. 571-580.
Altan-Yaycioglu R., et al., "Pseudo-accommodation with Intraocular Lenses Implanted in the Bag," Journal of Refractive Surgery, 2002, vol. 18 (3), pp. 271-275.
Chauvin-Opsia, Azurite ACL (0459).
Chiron, Clemente Opfit Model SP525, Brochure Translation, Jul. 12, 1998.
Cohen A. L., "Diffractive Bifocal Lens Design," Optometry and Vision Science, 1993, vol. 70 (6), pp. 461-468.
Cohen A.L., "Practical Design of a Bifocal Hologram Contact Lens or Intraocular Lens," Applied Optics, 1992, vol. 31 (19), pp. 3750-3754.
Co-pending U.S. Appl. No. 09/656,661, filed Sep. 7, 2000.
Foldable Intraocular Lens Implants and Small Incision Cataract Surgery, Ohio Valley Eye Physicians, 2004.
Hanita Lenses, Source Ocular Surgery News International, 1 page.
Hecht E., et al., "Optics", 4th Edition, Addison-Wesley Publishing Company, 1979, pp. 188-190.
Holladay J.T., et al., "A Three-Part System for Refining Intraocular Lens Power Calculations," Journal of Cataract and Refractive Surgery, 1988, vol. 14 (1), pp. 17-24.
Holladay J.T., et al., "Analysis of Edge Glare Phenomena in Intraocular Lens Edge Designs," Journal of Cataract and Refractive Surgery, 1999, vol. 25 (6), pp. 748-752.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
Klien S.A., "Understanding the Diffractive Bifocal Contact Lens," Optometry and Vision Science, 1993, vol. 70 (6), pp. 439-460.
Kuchle M., et al., "Implantation of a New Accommodative Posterior Chamber Intraocular Lens," Journal of Refractive Surgery, 2002, vol. 18 (3), pp. 208-216.
Lane S.S., et al., "Polysulfone Intracorneal Lenses," International Ophthalmology Clinics, 1991, vol. 31 (1), pp. 37-46.
Marron J.C., et al., "Higher-order Kinoforms," Computer and Optically Formed Holographic Optics, 1990, vol. 1211, pp. 62-66.
McCarey B.E, et al., "Modeling Glucose Distribution in the Cornea," Current Eye Research, 1990, vol. 9 (11), pp. 1025-1039.
Mediphacos Ltda, Ocular Surgery News International.
Opthalmed Inc., OMAC-260.
Prosecution History for U.S. Appl. No. 10/958,871, filed on Oct. 5, 2004.
Prosecution History for U.S. Appl. No. 11/057,705, filed on Feb. 14, 2005.
Prosecution History for U.S. Appl. No. 11/195,422, filed on Aug. 1, 2005.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Randall Woods D.O., "The Woods Concept for Capsular Bag Placement," Copeland Intra Lenses, Inc.
Storz Opthalmics Inc., Model L122UV ACL.
Taylor B.N., ed., The International System of Units (SI), 1991, NIST Special Publication 330, 4 pages.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
Universe IOL Center, Ocular Surgery News International.
VIDEO presented by ASCRS Symposium of Cataracts IOL and Refractive Surgery at the ASOA Congress on Ophthalmic Practice Management. Clinical & Surgical Staff Program on Apr. 10-14, 1999 (VHS Tape).
World Optics Inc., Ophthalmology Times, Mar. 15, 1995.

\* cited by examiner

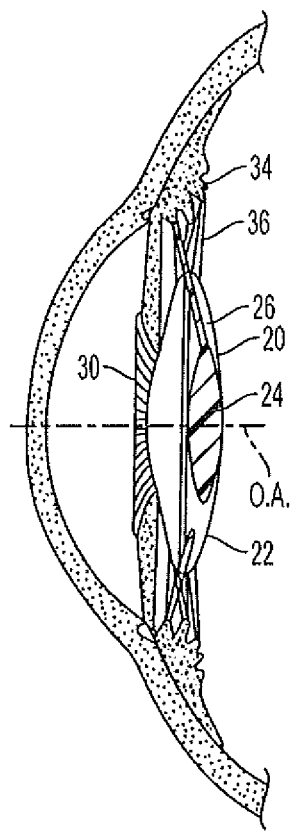
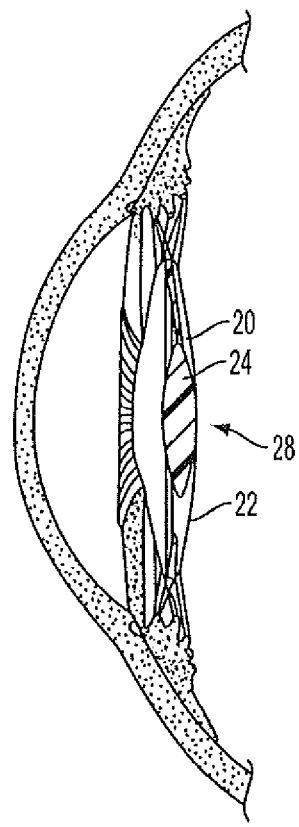
FIG. 1
FIG. 2
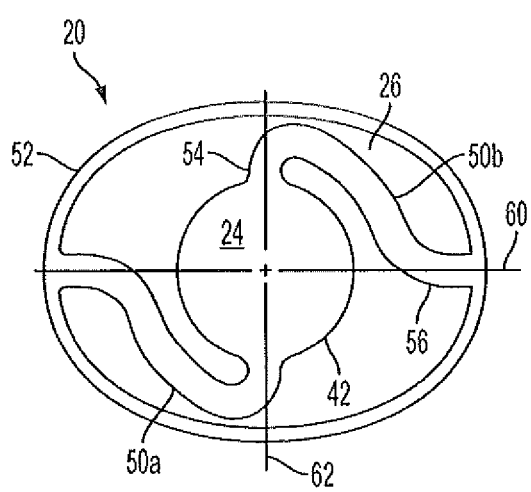
FIG. 3
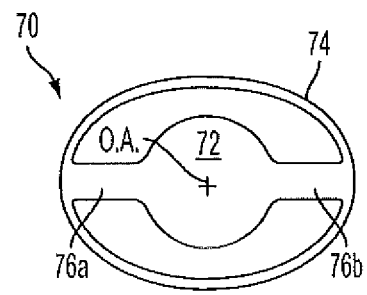
FIG. 4
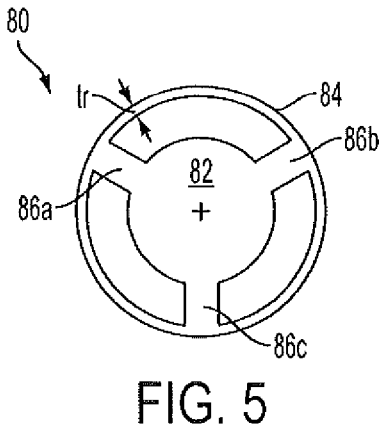
FIG. 5

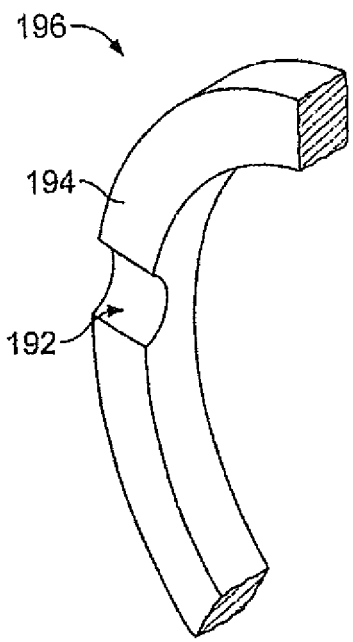
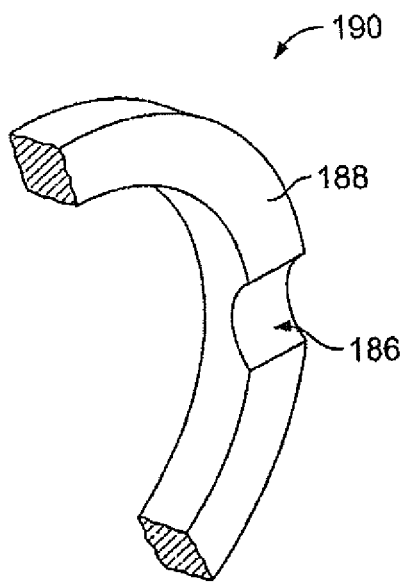
FIG. 15     FIG. 16
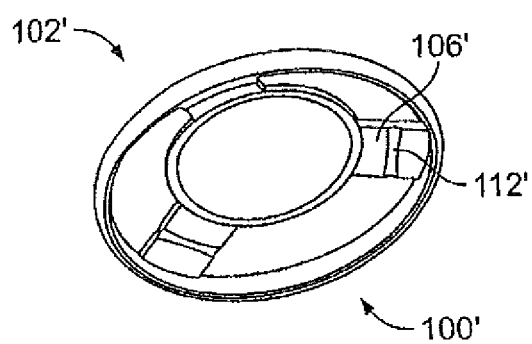
FIG. 17

ACCOMMODATING INTRAOCULAR LENS WITH OUTER SUPPORT STRUCTURE

RELATED APPLICATIONS

This application in a Divisional of U.S. patent application Ser. No. 12/840,843, titled "Accommodating Intraocular Lens with Outer Support Structure," filed on Jul. 21, 2010 which is a Continuation of U.S. patent application Ser. No. 11/322,068, titled "Accommodating Intraocular Lens with Outer Support Structure," filed on Dec. 28, 2005 which is a Continuation-In-Part of U.S. patent application Ser. No. 10/661,401, titled "Multi-Mechanistic Accommodating Intraocular Lens," filed Sep. 12, 2003, no U.S. Pat. No. 7,150,759, which is a Continuation-In Part of U.S. patent application Ser. No. 10/341,701, titled "Accommodating Intraocular Lens with Integral Capsular Bag Ring," filed Jan. 14, 2003, now U.S. Pat. No. 7,025,783, which claimed the benefit of provisional application Ser. No. 60/348,705, filed Jan. 14, 2002, and provisional application Ser. No. 60/372,309, filed Apr. 12, 2002. The disclosures of all of the above are incorporated herein by reference in their entirety.

BACKGROUND OF THE INVENTION

The present invention relates to intraocular lenses (IOLs). More particularly, the present invention relates to IOLs that provide accommodating movement in the eye.

The human visual system includes the eyes, the extraocular muscles which control eye position within the eye socket, the optic and other nerves that connect the eyes to the brain, and particular areas of the brain that are in neural communication with the eyes. Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape within the capsular bag, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber behind the lens. The crystalline lens is contained within a third chamber of the eye, the posterior chamber, which is positioned between the anterior and vitreous chambers.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by either changing the shape of at least one optic surface of the IOL, by moving the IOL along its optical axis, or some combination of the two. These and similar approaches for providing accommodation are disclosed, for example, in the following U.S. patents and patent applications, all of which are herein incorporated by reference: U.S. Pat. Nos. 4,373,218; 4,601,545; 4,816,031; 4,892,543; 4,994,083; 5,066,301; 5,108,429; 5,171,266; 5,203,788; 6,176,878; 6,406,494; 6,443,985; 6,599,317; 6,616,692; 6,638,305; 6,645,246; 2003/0060881; 2003/0158599; 2004/0034415; 2004/0082993; 2005/0131535; and U.S. patent application Ser. No. 09/656,661, filed in Sep. 7, 2000.

Despite these various devices and method of providing accommodation, there continues to be a need, to provide new IOLs with enhanced accommodative capabilities.

SUMMARY OF THE INVENTION

In one aspect of the invention, an intraocular lens for insertion into the capsular bag of an eye comprises an optic, an outer periphery, an outer support structure. The optic has a periphery and centered about an optical axis. The outer periphery is configured to engage an equatorial region of the capsular bag of an eye and the outer support structure is disposed along the outer periphery of the intraocular lens and is spaced from the optic with voids therebetween. The intraocular lens further comprises a first intermediate member operably coupled to the optic and the outer support structure. The intraocular lens also comprises first and second weakened regions disposed along the outer periphery. Each of the weakened regions may be disposed between the outer support structure and the first intermediate member. The weakened regions are configured to allow relative motion between the outer support structure and the first intermediate member in response to the ciliary muscle of the eye. In certain embodiments, the relative motion is an angular motion between the first intermediate member and the outer support structure.

In certain embodiments, the outer support structure surrounds or entirely surrounds the optic and/or the intermediate members. In other embodiments, the outer support structure is connected to distal ends of the first and second intermediate members. In such embodiments, the weakened regions are disposed along the outer periphery to either side of and/or proximal to the distal ends. The outer periphery may be circular or elliptical or some other shape that is suited for insertion into the eye, for example, into the capsular bag.

In another aspect of the invention, the intraocular lens further comprises a second, or even three or more, intermediate member(s) extending between and operably coupling the optic and the outer support structure. In such embodiments, the intraocular lens may comprise first weakened regions disposed along the outer periphery between the outer support structure and the intermediate members, as well as second weakened regions disposed along the outer periphery between the outer support structure and the intermediate members. The first and second weakened regions may be configured to allow angular motion between the outer support structure and the intermediate members in response to the ciliary muscle and/or capsular bag. In some embodiments, the outer support structure further comprises at least one intermediate weakened region circumferentially disposed between intermediate members. The intermediate weakened regions may be circumferentially disposed equidistant between intermediate members or otherwise disposed to provide a predetermined performance of the outer support structure or intraocular lens when the outer support structure is compressed or stretched.

The weakened regions may be configured or formed in various way to provide the predetermined performance of the outer support structure or intraocular lens. For example, one or more of the weakened regions may comprise a hinge. Also, one or more of the weakened regions may have a radial thickness that is less than a radial thickness of the outer support structure in a region proximal the at least one weakened region. Additionally or alternatively, the weakened regions may have a thickness along the optical axis that is less than a thickness along the optical axis of the outer support structure in a region proximal the at least one weakened region. In some embodiments, the outer support structure is made of a first material and at least one of the weakened regions is made of a second material that is more bendable than the first material.

In yet another aspect of the invention, the outer support structure comprises a first arm and the second arm with a void therebetween. In such embodiments, at least a portion of the first arm may be slidably disposed to at least a portion of the second arm.

Another aspect of the invention involves an intraocular lens for insertion into the capsular bag of an eye comprising an optic, an outer support structure having an outer periphery, a first intermediate member, and a weakened region disposed proximal to the first intermediate member and along the outer periphery of the intraocular lens. The optic has a periphery and is centered about an optical axis. The first intermediate member extends between and is operably coupled to the optic and the outer support structure. The outer support structure entirely and continuously surrounds the optic and is spaced from the optic and there are one or more voids between the outer support structure and the optic. The outer support structure is configured to engage an equatorial region of the capsular bag of an eye. The weakened region is configured to allow relative motion between the outer support structure and the first intermediate member in response to the ciliary muscle of the eye.

Each and every feature described herein, and each and every combination of two or more of such features, is included within the scope of the present invention provided that the features included in such a combination are not mutually inconsistent.

BRIEF DESCRIPTION OF THE DRAWINGS

Additional aspects, features, and advantages of the present invention are set forth in the following description and claims, particularly when considered in conjunction with the accompanying drawings in which like parts bear like reference numbers.

FIG. 1 is a vertical cross-section of an eye illustrating an exemplary intraocular lens of the present invention positioned within the capsular bag;

FIG. 2 is a cross-section similar to FIG. 1 showing forward or anterior movement of an optic of the intraocular lens;

FIG. 3 is a plan view of the exemplary intraocular lens of the present invention having an oval outer ring and a pair of nonlinear intermediate members;

FIG. 4 is a plan view of an alternative intraocular lens of the present invention having two radially oriented intermediate members;

FIG. 5 is a plan view of an alternative intraocular lens of the present invention having three radially oriented intermediate members;

FIG. 15 is a fragmentary perspective posterior view showing a portion of a support ring structured to bend in an anterior direction;

FIG. 16 is a fragmentary perspective anterior view showing a support ring structured to bend in a posterior direction;

FIG. 17 is a view similar to FIG. 7B, showing an embodiment of the invention having an alternate hinge configuration;

DETAILED DESCRIPTION OF THE DRAWINGS

Figure 6:
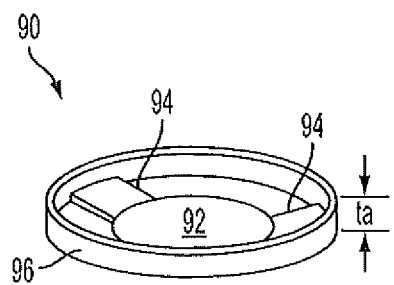
FIG. 6 is a perspective view of an alternative intraocular lens of the present invention having three radially oriented intermediate members.

Referring to the drawings in more detail, an intraocular lens (IOL) 20 according to an exemplary embodiment of the present invention is illustrated in FIGS. 1 and 2 after implantation in the capsular bag 22 of an eye. Exemplary IOL 20 includes an optic 24 and a movement assembly 26 coupled thereto. The optic 24, which has an optical axis OA, is adapted to focus light onto a retina of an eye. The movement assembly 26 of exemplary IOL 20 cooperates with the eye to effect accommodating movement of the optic 24 and, in particular, converts radial movement (i.e., movement perpendicular to the optical axis OA) of the capsular bag of an eye to axial movement (i.e., movement parallel to the optical axis OA) of the optic 24. In the exemplary embodiment, the movement assembly 26 biases the optic 24 in a posterior direction (to the right) against the posterior wall of the capsular bag 22.

With further reference to FIG. 3, which illustrates the exemplary IOL 20 in plan view, the optic 24 comprises a generally circular periphery or peripheral edge 42 that defines the radially outer extent of the optic 24 and separates a posterior face from an anterior face. The optic 24 is typically circular, but may exhibit a different shape as long as the optical correction character is centered about the optical axis OA. The optic 24 may be bi-convex, or the anterior and posterior faces can take other shapes, such as planar or concave. In any event, the posterior face and anterior face are spaced apart on opposite sides of an optic plane (not shown) that extends perpendicular to the optical axis OA. In other words, the optic 24 is centered on and oriented in the optic plane.

The movement assembly 26 may further comprise a pair of intermediate members 50a, 50b connected to and extending between the circular periphery 42 of the optic 24 and an outer ring 52. Each intermediate member 50a, 50b has an inner end 54 connected to the circular periphery 42, and an outer end 56 connected to the outer ring 52. As used herein in this context, the term "connected" means firmly attached to, for example, by using an adhesive or ultrasonic bond, by forming integrally, or by forming as a cohesive single piece. In the latter case, the lens is desirably molded. Each intermediate member 50a, 50b is desirably oriented in a plane that is in the optic plane. Indeed, the intermediate members 50a, 50b and outer ring 52 may have approximately the same thickness and be located in the same plane.

A brief description of the anatomy of the eye is appropriate in order to understand the invention. The capsular bag 22 resides in the posterior chamber of the eye and is in direct contact with the jelly-like vitreous humor 28 which fills the nearly spherical space between the capsular bag and the retina (not shown). In a healthy person, the capsular bag 22 contains the natural crystalline lens which transmits light passing through the orifice of the iris 30 to the retina. The capsular bag 22 is connected to an annular ciliary muscle 34 by suspensory ligaments or zonules 36. The ciliary muscle 34 is the chief agent in accommodation, i.e., in adjusting the eye to focus on near objects. The zonules 36 retain the lens in position and are relaxed by the contraction of the ciliary muscle 34, thereby allowing a natural crystalline lens to become more convex.

In certain embodiments, the optic 24 is monofocal optic. In such embodiments, the anterior and posterior surfaces of the optic 24 may have spherical profiles. Alternatively, at least one of the anterior and posterior surfaces of the optic 24 may have an aspheric profile, for example, as discussed in U.S. Pat. No. 6,609,793, which is herein incorporated by reference. In other embodiments, the optic 24 is a multifocal optic having a plurality of zones of varying optical powers, wherein the maximum add power of the near zones is reduced by an amount equivalent to the diopter shift obtained through axial movement of the optic 24. Thus, the net power correction in the near zones is equal to the patient's full add prescription only when optic 24 has moved to the near distance (i.e., anteriormost) position. Examples of suitable multifocal optics are disclosed in Lang et al. U.S. Pat. No. 6,231,603 and Lang et al. PCT International Application No. WO/01/82839 A1. The disclosures of both the U.S. patent and the PCT international application are incorporated in their entireties herein by reference.

Although controlled fibrosis (i.e., cellular growth) on the outer ring 52 may be desirable, the IOLs 20 of the invention inhibit cell growth, particularly epithelial cell growth, onto the optic 24. This is accomplished by configuring the periphery 42 of the optic 24 with mechanical barriers such as relatively sharp posterior and/or anterior edge corners, for example, as disclosed in U.S. Pat. Nos. 6,162,249, 6,468, 306, and 6,884,262. The proliferation of unwanted epithelial cell growth may also be inhibited through the use of material properties.

The intermediate members 50a, 50b of the IOL 20 are substantially longer than previous intermediate members as they extend in a nonlinear fashion from the outer ring 52 to the circular optic periphery 42. More particularly, the inner end 54 and outer end 56 are angularly spaced about the optical axis OA by at least approximately 90 degrees. The mid-portion of each intermediate member 50 extends in a serpentine fashion between its inner and outer ends.

In certain embodiments, as seen in FIG. 3, the outer ring 52 is oval in shape and has a major axis 60 perpendicular to the optical axis OA. A minor axis 62 extends perpendicularly to the major axis 60 and to the optical axis OA. Desirably, the outer ends 56 of the intermediate members 50 connect to the oval ring 52 along the major axis 60. In this way, the length of the intermediate members 50 is maximized. In the illustrated embodiment, the inner ends 54 of the intermediate members 50 connect to the circular optic periphery 42 along the minor axis 62. Therefore, the inner and outer ends 54, 56 are angularly spaced apart by about 90 degrees.

FIG. 4 illustrates an alternative IOL 70 of the present invention having an optic 72, an oval outer ring 74, and a pair of intermediate members 76a, 76b extending radially therebetween. Again, the optic 72, outer ring 74 and intermediate members 76a, 76b are desirably formed as a single homogeneous (i.e., integral) piece. In certain embodiments, the oval outer ring 74 may move the optic 72 axially with greater effectiveness than a circular ring because of the orientation of the intermediate members 76 *a, b* along the major axis.

The fixation members 76 *a, b* are shown as plate-like, and desirably are greater in width (the dimension parallel to the minor axis) than axial thickness (the dimension parallel to the optical axis). Preferably, the ratio of width to axial thickness is about four. In absolute terms, the width of the fixation members 76*a*, 76*b* may be between about 0.8 mm and about 3.0 mm.

FIG. 5 illustrates a still further IOL 80 having an optic 82, an outer ring 84, and three evenly arranged and radially oriented intermediate members 86*a*, 86*b* and 86*c*. Because the intermediate members 86 are not symmetric about any plane through the optical axis OA, forces exerted by the surrounding capsular bag do not act in opposition to one another and thus may be translated more effectively into axial movement of the optic 82. The radial thickness $t_r$ of the outer ring 84 is indicated, and is desirably in the range of 0.2-0.6 mm. Moreover, the corners, or at least one corner, of the outer peripheral edge of the outer ring 84 are desirably relatively sharp to reduce the instance of epithelial cell growth thereon.

Figure 6A:
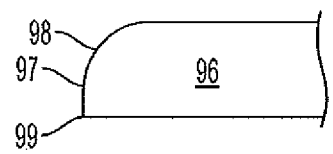
FIG. 6A is an elevational view of one edge of the intraocular lens of FIG. 6.

FIGS. 6 and 6A illustrate a still further IOL 90 of the present invention having an optic 92, a plurality of intermediate members 94 extending radially outward therefrom, and an outer ring 96. The edge surface 97 of the outer ring 96 may be contoured to conform to the inner wall of the capsular bag. Therefore, as seen in FIG. 6A, at least a portion 98 of the edge surface 97 is convexly outwardly curved. At the same time, at least one corner, in this case the posterior corner 99, is left sharp (i.e., unpolished) to form a barrier against posterior capsular opacification (PCO).

Furthermore, FIG. 6 illustrates the greater axial thickness $t_a$ of the outer ring 96 with respect to the axial thickness of the intermediate members 94 and optic 92. Specifically, the axial thickness $t_a$ of the outer ring 96 is desirably between about 0.4 mm and about 1.0 mm. Without wishing to limit the invention to any particular theory of operation, it is believed that a ring having an axial thickness in this range will place both the posterior and the anterior zonules of the eye under tension. Thus, both sets of zonules work in unison to change the diameter of the capsular bag in response to action of the ciliary muscle, resulting in axial movement of the optic. In some embodiments, a thinner ring would not interact as effectively with both sets of zonules, and thus, in all likelihood, would result in less axial movement.

In addition, an outer ring 96 having increased axial thickness will increase the pressure on the sharp corner 99 of the edge surface 97 to increase the barrier effect of the ring against PCO.

FIGS. 7A-7E show another IOL 100 of the present invention having a circular outer capsular bag support ring 102, an inner optic 104, and a movement system comprising a plurality of radially-oriented plate-like intermediate members 106 extending therebetween. Preferably, the optic 104, whether it be bi-convex or otherwise, is circumscribed by a circular rim 105 to which the fixation intermediate members 106 are directly attached. The rim 105 desirably has a constant axial dimension and helps to reduce glare while not increasing incision size.

Movement systems other than that shown may be suitable, such as a more solid interface rather than discrete intermediate members. However, separated intermediate members with voids therebetween and between the optic 104 and support ring 102 are preferred. The support ring 102, inner optic 104, and intermediate members 106 are firmly attached to each other with adhesive or ultrasonic bonding, or preferably formed integrally, i.e., molded or machined as one cohesive (homogeneous) piece of material. The IOL 100 is desirably liquid injection molded from silicone or machined from a hydrophilic material which fabrication process reduces cost and increases quality and/or consistency of the product.

Figure 7A:
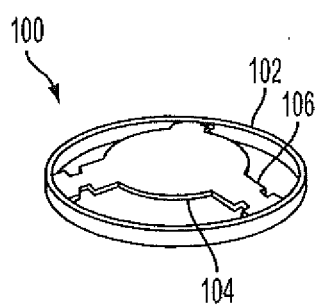
FIG. 7A is a perspective posterior view of a still further alternative intraocular lens of the present invention having three radially oriented plate-like intermediate members and an optic that is bowed slightly out of the plane of a surrounding capsular bag support ring.
Figure 7B:
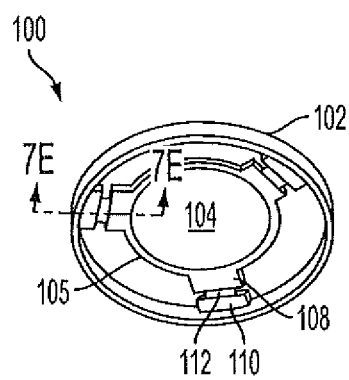
FIG. 7B is a perspective anterior view of the intraocular lens of FIG. 7A.

FIG. 7A illustrates the IOL 100 from the posterior side, while FIG. 7B is an anterior view. These two views show the axial position at which the intermediate members 106 attach to the support ring 102. That is, the support ring 102 has an axial dimension and the intermediate members 106 attach to a posterior edge thereof. When implanted, the intermediate members 106 and connected optic 104 are therefore held in a posterior-most position with respect to the support ring 102.

As in the embodiment of FIG. 6, the edge surface of the outer ring 102 is contoured to facilitate implantation within the capsular bag of the patient. More particularly, the support ring 102 has an outer surface that is convexly curved to better mate with the concave inner wall portion of the capsular bag between the anterior and posterior zonules.

Figure 7C:
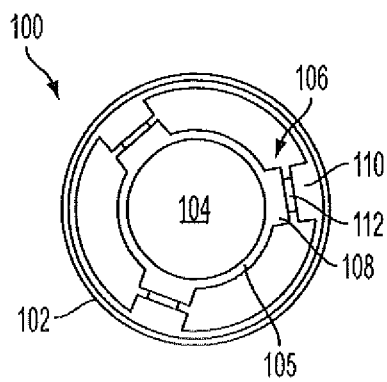
FIGS. 7C and 7D are plan and side elevational views, respectively, of the intraocular lens of FIG. 7A.
Figure 7D:
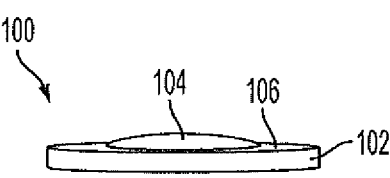
Figure 7E:
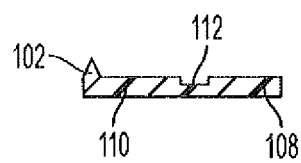
FIG. 7E is a sectional view taken through line 7E-7E of FIG. 7B.

With reference to FIGS. 7C and 7E, the intermediate members 106 comprise a radially inner portion 108, a radially outer portion 110, and a hinge 112 therebetween. The inner and outer portions 108, 110 are generally plate-like having larger circumferential dimensions than axial dimensions. The hinge 112 may be formed in a number of ways, and as illustrated comprises a region wherein both the axial and the circumferential thickness are reduced by about 50% with respect to the inner and outer portions 108, 110. Alternatively, only one of the axial and the circumferential thicknesses are reduced as compared to the remaining portions of the intermediate member 106. The reduced material at the hinge 112 means that it is weaker than the remaining portions of the intermediate member and thus will more easily bend at that location. In other embodiments, the hinge 112 has the same axial and the circumferential thickness as the remaining portions of the intermediate member 106. In such embodiments, the hinge 112 may be made of a different material or from the same material that is processed differently from the remaining portions of the intermediate member 106 (e.g., with a differing amount of polymerization). The location of each hinge 112 is desirably the same for all of the fixation intermediate members 106, and preferably is closer to the support ring 102 than to the optic 104. For example, each hinge 112 may be located about 60% of the way from the optic 104 to the support ring 102. In some embodiments, the intermediate member 106 has no distinct hinge such as the hinge 112, for example, as illustrated in FIGS. 4 and 5 for the IOLs 70 and 80, respectively. In such embodiments, the entire intermediate member (e.g., intermediate members 76*a* or 86*a*) may bend to allow the optic of the IOL to translate anteriorly and posteriorly in response to the ciliary muscle 34.

FIG. 7D illustrates the IOL 100 in an elevational view wherein the support ring 102 lies substantially in a plane and the optic 104 projects in a posterior direction therefrom by virtue of the shape of the intermediate members 106. Specifically, the intermediate members 106 are bowed slightly in the posterior direction such that the optic 104 will tend to lie against or closely adjacent to the posterior wall of the capsular bag. Relaxation of the ciliary muscles 34 surrounding the capsular bag 22 either moves the optic 104 or changes the posterior bias imparted thereto by the intermediate members 106. As a result, the vitreous humor behind the capsular bag can move the optic 106 so as to allow a subject to focus both on distant and relatively near objects.

In one exemplary embodiment, the support ring 102 has a diameter of between about 9.0-10.5 mm, and an axial thickness of about 0.7 mm. Furthermore, the support ring 102 has a curvature that mimics the curvature of the natural capsular bag between the anterior and posterior zonules, which curvature is between about 0.3-1.0 mm. As mentioned above, at least one corner edge of the outer ring is left sharp to help prevent cell growth thereon. In other embodiments, the support ring 102 may be sized to have a diameter that provides a predetermined fit within the capsular bag 22, for example when the eye is in an accommodative state, a disaccommodative state, or a state somewhere between the accommodative and disaccommodative states. IOLs 100 may be configured to have a plurality of diameters to provide a predetermined fit within different size capsular bags 22 for different eyes. Preferably, the diameter of the support ring 102 is between about 8 mm and at least about 13 mm, more preferably between 8 mm and 12 mm, and even more preferably between 9 mm and 11 mm.

Although three radial intermediate members 106 are illustrated 120 degrees apart, the configuration of the intermediate members 106 may vary. However, two factors that are believed to facilitate axial movement, or accommodation, of the optic 104 are the tripod orientation and presence of the hinges 112. More specifically, inward radial forces from the surrounding ciliary muscle 34 and intermediary zonules 36 are transmitted from the support ring 102 through the intermediate members 106 to the optic 104. Because the intermediate members 106 are oriented so that none is diametrically opposed to another, there are no directly opposing forces and a larger component therefore translates into axial movement of the optic 104.

The intermediate members 106 are plate-like to increase stability of the lens in the eye. That is, the forces imparted by the surrounding ciliary muscle 34 may not be entirely uniform and may exert torsional forces on the lens. Plate-like intermediate members 106 help resist twisting of the lens and thus increase stability. The circumferential thickness, or width, of the intermediate members 106 may be between about 1.5-4.0 mm, and the axial thickness is desirably between about 0.2-0.5 mm.

FIG. 17 shows an alternate embodiment of an IOL 102' substantially similar to the embodiment of FIGS. 7A-7E, except that the thickness of the hinge portion 112' is reduced in the axial direction only. That is, the circumferential thickness, or width, of each plate-like intermediate member 106' is uniform throughout its length. This hinge configuration has been found to be less susceptible to fibrosis than a hinge configuration having reduced thickness in the circumferential direction.

Another alternative IOL 120 of the present invention is seen in FIGS. 8A-8D. As in an earlier embodiment, there are only two intermediate members 122 extending between an oval shaped outer capsular bag support ring 124 and an inner circular optic 126. In the illustrated embodiment, the outer ring 124 comprises a band having a generally rectangular cross-section with a longer axial than radial dimension. Preferably, at least one corner of the outer ring 124 is sharp to prevent epithelial cell growth thereon. The support ring 124, inner optic 126, and intermediate members 122 are firmly attached to each other with adhesive or ultrasonic bonding, or preferably formed integrally, i.e., molded or machined as a cohesive single piece. The IOL 120 is desirably liquid injection molded from silicone or machined from a hydrophilic material which, again, reduces cost and increases quality and/or consistency of the product.

Figure 8A:
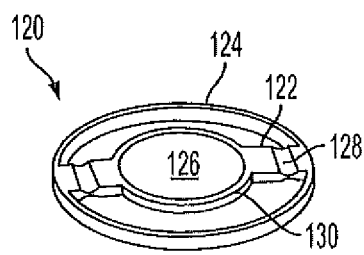
FIG. 8A is a perspective view of a still further alternative intraocular lens of the present invention having two radially oriented plate-like intermediate members connecting a central optic to an oval surrounding capsular bag support ring.
Figure 8B:
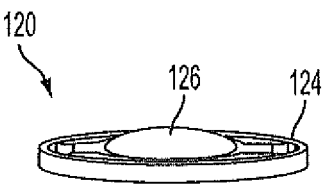
FIG. 8B is another perspective view of the intraocular lens of FIG. 8A.
Figure 8C:
FIGS. 8C and 8D are side elevational and plan views, respectively, of the intraocular lens of FIG. 8A.
Figure 8D:
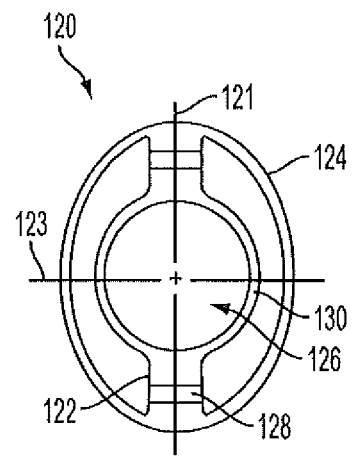

As seen best in FIG. 8D, the oval outer ring 124 has a major axis 121 and a minor axis 123, and the two intermediate members 122 are diametrically opposed across the optic 126 along the major axis 123. In one exemplary embodiment, the support ring 124 has a major diameter of between about 115-135% of the minor diameter.

The intermediate members 122 are plate-like, each having a relatively larger circumferential than axial dimension. In contrast to the IOL 100 of FIGS. 7A-7D, the intermediate members 122 lie in a plane defined by the oval-shaped outer ring 124, and thus the optic 126 is not bowed either way. Furthermore, the intermediate members 122 are joined to the inner surface of the outer ring 124 at approximately the axial midpoint thereof. Therefore, in contrast to the earlier embodiment, the optic 126 is not positioned or biased to favor movement in one direction or the other.

With reference to FIG. 8A, each intermediate member 122 has a hinge 128 therein located closer to the outer ring 124 than to the optic 126. The location of each hinge 128 is desirably the same for all of the intermediate members 122, and preferably is located about 75% or more of the way from the optic 126 to the support ring 124. Empirical determination of hinge 128 location optimizes the design such that less radial and axial compression force is required to axially translate the optic 126, while at the same time the ability of the lens to resist twisting is not adversely affected. In the illustrated embodiment, these hinges 128 are formed by reduced axial thickness portions along each intermediate member 122. For example, curved troughs on both sides of intermediate members 122 as shown may form the hinges. Alternatively, or in addition, the circumferential dimension of each intermediate member 122 may be reduced.

As with the earlier embodiment, the optic 126, whether it be biconvex or otherwise, is recessed from a circular rim 130 to which the intermediate members 122 are directly attached. The rim 130 is slightly tapered downward toward the optic and helps reduce glare on the lens. Desirably, the maximum axial dimension of the rim 130 is greater than the center thickness of the optic 126. Advantageously, a reduced center thickness permits a reduction in incision size.

Figure 18A:
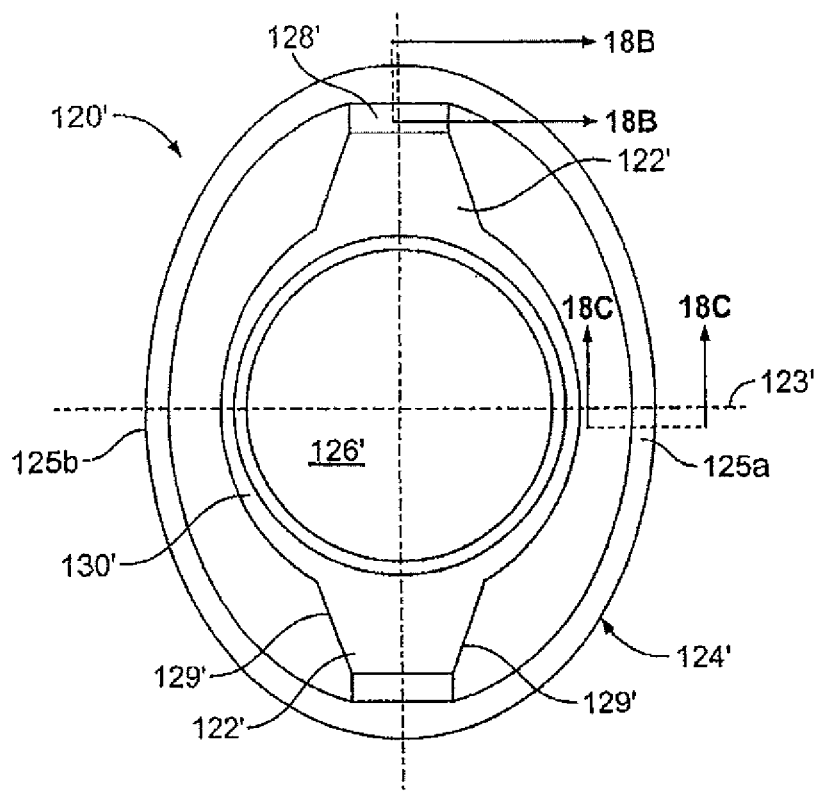
FIG. 18A is an anterior plan view showing yet another embodiment of an intraocular lens according to the present invention.
Figure 18B:
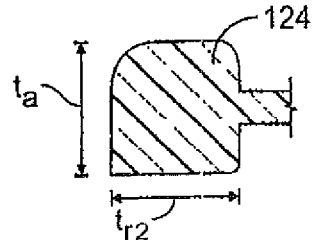
FIG. 18B is a sectional view taken through line B-B of FIG. 18A.
Figure 18C:
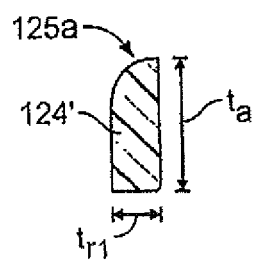
FIG. 18C is a sectional view taken through line C-C of FIG. 18A.

FIGS. 18A-18C show an alternate embodiment of an IOL 120' similar to the embodiment of FIGS. 8A-8D, except that the optic 126' is multifocal, and oval support ring 124' has a non-uniform cross-sectional area. Alternatively, the optic 126' may be a monofocal optic, as discussed elsewhere herein. In the illustrated embodiment, the radial thickness of the support ring 124' increases from a minimum value $t_{r1}$, for instance about 0.2 mm, at diametrically opposed locations 125a and 125b along the minor axis 121', to a maximum value $t_{r2}$, for instance about 0.6 mm, at diametrically opposed locations along the major axis 123', where the intermediate members 122' are secured to the ring 124'. In addition, the axial thickness $t_a$ of the ring 124' is constant throughout the entire circumference of the ring 124' and has a value greater than the maximum radial thickness $t_{r2}$.

The circumferential thickness, or width, of each intermediate member 122' is also non-uniform throughout its length, for instance decreasing in a non-linear fashion from a maximum width where the intermediate member 122' joins the circular rim 130' of the optic 126' to a minimum width at the hinge 128', and remaining substantially constant between the hinge 128' and the outer ring 124'. This particular configuration of the oval outer ring 124' and intermediate members 122' has been found to be particularly stable, with minimal "flopping", twisting, or other unwanted movement, of the thinnest portions 125a and 125b of the outer ring 124'.

FIGS. 9-16 and 19-25 show alternate embodiments of the invention wherein the support ring includes weakened portions configured to allow the ring to allow consistent and repeatable deformation during compression.

Figure 9:
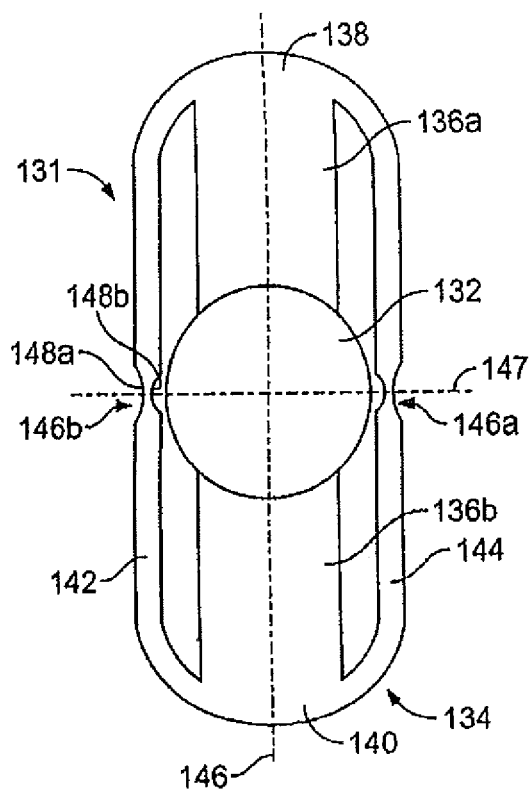
FIG. 9 is a plan view of another alternate embodiment of the invention.

FIG. 9 shows an IOL 131 having an optic 132, an outer ring 134, and a pair of plate-like intermediate members 136a and 136b. The intermediate members 136a and 136b are shown without hinges, similar to the intermediate members 76a and 76b of FIG. 4, although hinged intermediate members could also be used. The outer ring 134 is generally oval, with two generally arcuate ends 138, 140 that merge with the distal ends of the intermediate members 136a and 136b, respectively, and two elongated leg portions 142, 144 that extend parallel to a major axis 146 of the outer ring 134 along opposite sides of the optic 132

A weakened portion 146a, b is formed in each leg portion 142, 144 at a location along the minor axis 147 of the support ring 134, such that each weakened portion 146a, b is 180 degrees away from the other weakened portion 146a, b and equidistant from the arcuate ends 138, 140 of the outer ring 134. Each weakened portion 146a, b is in the form of a thinned area in one of the legs 142, 144, the thinned area being created, in this embodiment, by providing a generally C-shaped indentation 148a, b on each side of the leg. This configuration ensures that any bending or buckling of the outer ring 134 as a result of compressive forces on the distal ends 138, 140 of the outer ring 134 will occur at the weakened portions rather than elsewhere along the outer ring 134. In some embodiments, the outer ring 134 comprises only one of indentations 148a, b. In yet other embodiments, the outer ring 134 comprises two or more weakened portions 146a and two or more weakened portions 146b in order cause the outer ring 134 to deform in a predetermined manner in response to the ciliary muscle 34. In such embodiments, the shape of each of at least some of the weakened portions 146a, b may be different from the shape of others of the weakened portions 146a, b in order to produce the desired response to the ciliary muscle 34.

Figure 10:
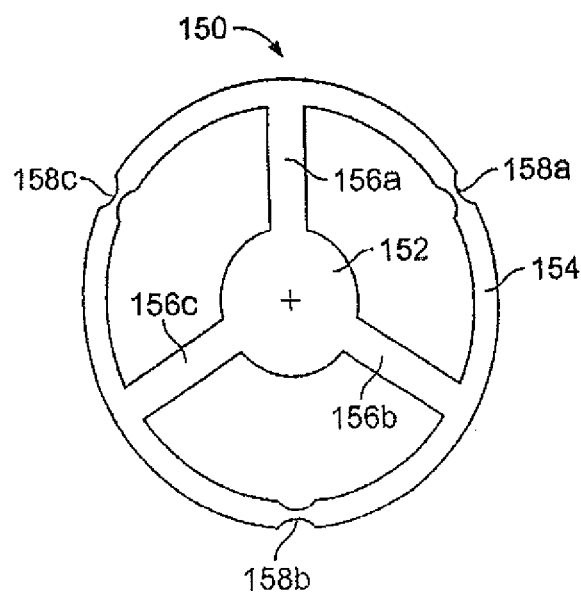
FIG. 10 is a plan view of still another alternate embodiment of the invention.

FIG. 10 shows an IOL 150, generally similar to IOL 80 of FIG. 5, comprising an optic 152, a circular outer ring 154 and three evenly arranged and radially oriented intermediate members 156a, 156b, and 156c, which may be hingeless as shown, or hinged, for example, as in the embodiment of FIGS. 7A-7D. The support ring 154 includes three weakened areas 158a, b, c provided 120 degrees from one another and radially equidistant from the intermediate members 156a, 156b, and 156. Again, the weakened areas 158a, b, and c, which are shown here as C-shaped indentations on each side of the outer ring 154, are configured to ensure that any bending or buckling of the outer ring 154 occurs at the three weakened area only, rather than at other locations along the ring. In some embodiments, there may be two or more weaken areas 158a, b, and c between each of the intermediate members 156a, 156b, and 156c in order to the outer ring 154 to deform in a predetermined manner in response to the ciliary muscle 34.

Figure 11:
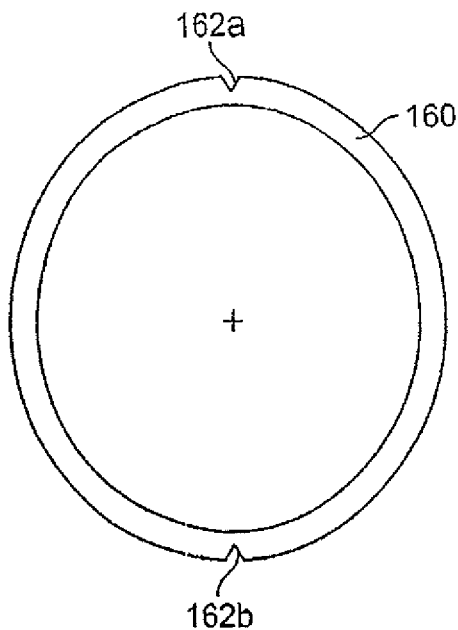
FIG. 11 is a plan view of an outer ring according to yet another embodiment of the invention.

FIG. 11 shows an outer ring 160 according to an alternate embodiment of the invention wherein the weakened areas 162a and 162b are in the form of V-shaped indentations or grooves in the outer circumferential surface 163 of the outer ring 160. An outer ring 160 having this configuration will tend to bend or buckle in a radially inward direction at the two weakened areas 162a and 162b when the outer ring 170 is subjected to compressive forces.

Figure 12:
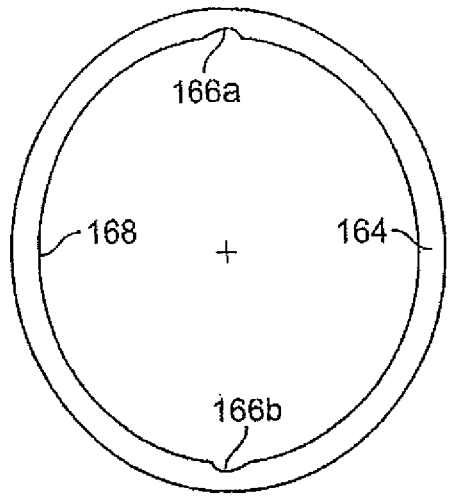
FIG. 12 is a plan view of an outer ring according to another embodiment of the invention.

FIG. 12 shows an outer ring 164 according to another embodiment of the invention wherein the weakened areas 166a and 166b are in the form of U-shaped indentations or grooves formed in the inner circumferential surface 168 of the outer ring 164. An outer ring 164 having this configuration will tend to bend or buckle in a radially outward direction at the two weakened areas 166a and 166b when the outer ring 164 is subjected to radially compressive forces.

Figure 13:
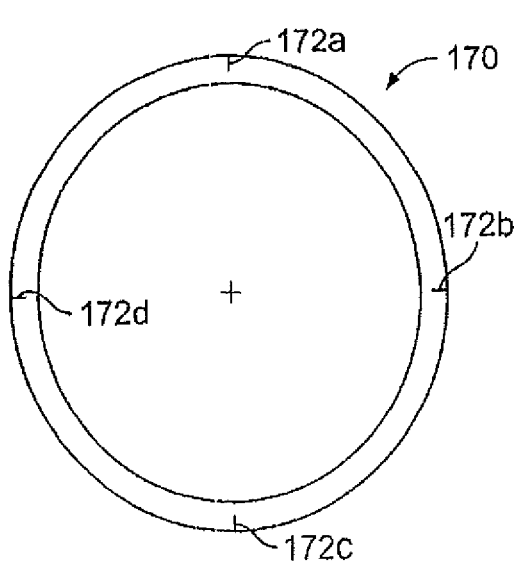
FIG. 13 is a plan view of a outer ring according to still another embodiment of the invention.

In still another embodiment of the invention, shown in FIG. 13, the outer ring 170 is provided with four symmetrically arranged weakened areas 172a, b, c, and d, each in the form of a slit or notch in the outer circumferential surface 174 of the outer ring 170. An outer ring 170 having this configuration will tend to bend or buckle in a radially inward direction at the four weakened areas when the outer ring 170 is subjected to radially compressive forces.

Figure 14:
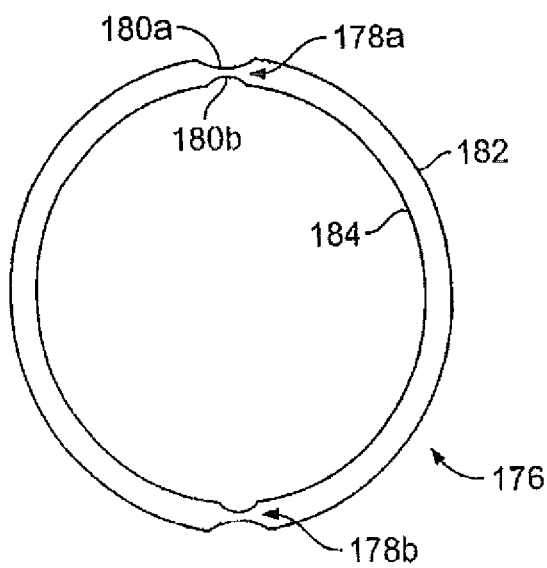
FIG. 14 is a plan view of a outer ring according to still another embodiment of the invention.

In yet another embodiment, shown in FIG. 14, a circular outer ring 176 is provided with two thinned areas 178a and 178b on diametrically opposite locations on the ring. Each thinned area is formed by providing a pair of U-shaped grooves or indentations in the ring 176, each pair consisting of a first indentation 180a in the outer circumferential surface 182 of the outer ring 176 and a second indentation 180b in the inner circumferential surface 184 of the outer ring 176.

FIG. 15 is an enlarged fragmentary perspective view showing a weakened portion 186 according to still another embodiment of the invention. In this embodiment, the weakened portion 186 comprises a thinned area, notch, indentation or groove formed in the posterior face 188 of the outer ring 190. An outer ring 190 having a plurality of weakened portions 186 configured in this way will tend to bend in an anterior direction (towards the cornea) at each of the weakened portions when subjected to radially compressive forces.

Alternatively, a weakened portion 192 according to another embodiment of the invention may comprise a thinned area, notch, indentation or groove formed in the anterior face 194 of the outer ring 196, as shown in FIG. 16. An outer ring 196 having a plurality of weakened portions 192 configured in this way will tend to bend in an posterior direction (away from the cornea) at each of the weakened portions when subjected to radially compressive forces.

Figure 19:
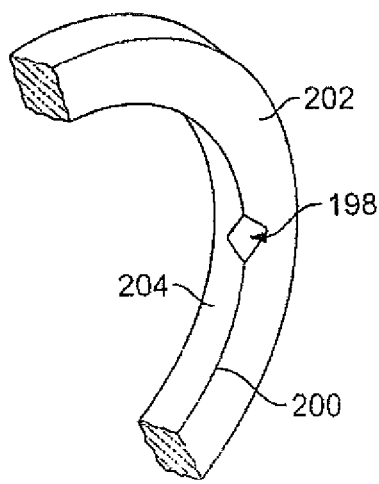
FIG. 19 is a fragmentary perspective anterior view showing a support ring structured to bend both posteriorly and radially outwardly.

FIG. 19 shows yet another embodiment of the invention wherein a weakened portion 198 is configured to cause bending in both a posterior and a radially outward direction. Although the weakened portion 198 is shown as a single notch formed at the corner 200 between the anterior surface 202 and the inner circumferential surface 204, it could also be formed as a pair of intersecting notches, grooves or indentations, one extending entirely across the anterior surface 202 and the other extending entirely across the inner circumferential surface 204, or any other equivalent configuration.

A weakened portion or portions could also be formed on any other combination or intersection of surfaces, for instance at a corner between a posterior surface and an outer circumferential surface to cause bending in anterior and radially inward directions, or at a corner between an anterior surface and an outer circumferential surface to cause bending in posterior and radially inward directions. Various other combinations of weakened portions will be readily apparent to the skilled practitioner, but for reasons of brevity will not be illustrated here.

Figure 20:
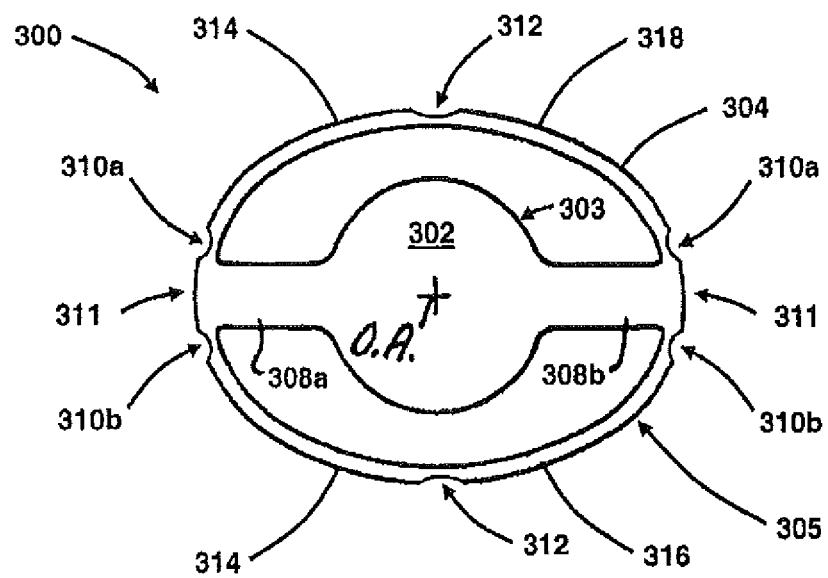
FIG. 20 is a plan view of an IOL having weakened portions according to embodiments of the present invention.

FIG. 20 illustrates still another embodiment of the invention wherein an IOL 300 comprises an optic 302 having a periphery 303 and centered about an optical axis OA, an outer support structure 304 disposed about the optic 302 and spaced therefrom, and first and second intermediate members 308a, 308b extending between and operably coupling (and/or directly connected to) the optic 302 and the outer support structure 304. The outer support structure 304 is disposed along an outer periphery 305 of the IOL 300 and is configured to engage an equatorial region of the capsular bag 22. The outer support structure 304 may entirely and continuously surround the optic 302. That is, the outer support structure 304 may form a closed or unbroken ring or loop completely around the optic 302. In some embodiments, the outer support structure 304 is coupled or attached to the first and/or second intermediate members 308a, b. For example, the outer support structure 304 may be connected to distal ends 311 of the first and second intermediate members 308a, b. In such embodiments, the weakened regions 310a, b may be disposed along the outer periphery 305 to either side of and/or proximal to the distal ends 311.

The IOL 300 further comprises one or more weakened regions, for example, the first and second weakened regions 310a, b shown in FIG. 20, disposed along the outer periphery 305 between the outer support structure 304 and the first and second intermediate members 308a, b. The first and second weakened regions 310a, b are attached to the outer support structure 304 and the first and second intermediate members 308a, b. The first and second weakened regions 310a, b are also configured to provide relative motion between the outer support structure 304 and the first and second intermediate members 308a, b in response to the ciliary muscle 34.

The weakened regions 310a, b are generally configured to allow angular motion between the first intermediate member 308a and the outer support structure 304 in response to the ciliary muscle 34. Depending upon the structure of the weakened regions 310a, b and the nature and direction of the forces applied to the IOL 300 by the ciliary muscle 34 and/or the capsular bag 22, the weakened regions 310a, b may additionally or alternatively allow relative linear motion between the between the first intermediate member 308a and the outer support structure 304 in response to the ciliary muscle 34.

Figure 21:
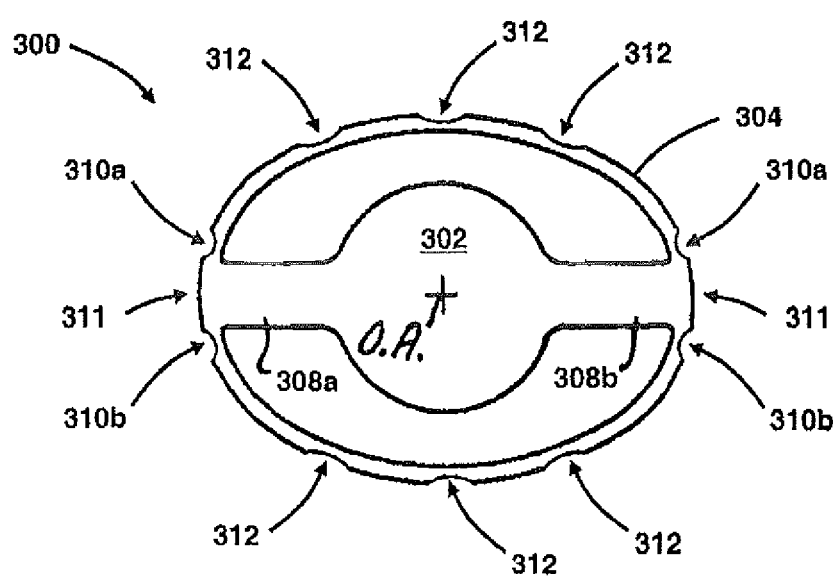
FIG. 21 is a plan view of another embodiment of an IOL having weakened portions.

With additional reference to FIG. 21, the outer support structure 304 may further comprise one or more intermediate weakened regions 312 that are circumferentially disposed between first and/or second intermediate members 308a, b. The intermediate weakened regions 312 may be disposed at locations on the outer support structure 304 that will allow the outer support structure 304 to bend, buckle, or otherwise deform in a predetermined and/or desirable manner when the IOL 300 is compress by the capsular bag 22 or is otherwise affected by force produced in response to the ciliary muscle 34. The weakened regions 310a, b and 312 may also be disposed so as to prevent or reduce unwanted deformation and/or twisting of either the optic 302 and/or the first and second intermediate members 308a, b.

The weakened regions 310a, b and intermediate weakened regions 312 may comprise various structures and/or material so as to provide a predetermined performance, bending, compression, and/or motion of the outer support structure 304 and the intermediate members 308a, b in response to the ciliary muscle 34 and/or the capsular bag 22. For example, any of the configurations or arrangements shown in FIGS. 9-16 may be used in conjunction with the IOL 300. Referring to the embodiments illustrated in FIGS. 20 and 21, one or more of the weakened regions 310a, b and 312 may have a radial thickness that is less than a radial thickness of the outer support structure in a region proximal the one or more weakened regions 310a, b and 312. Additionally or alternatively, one or more of the weakened regions 310a, b and 312 are disposed on a top or bottom surface of the outer support structure 304 and have a thickness along the optical axis OA that is less than a thickness along the optical axis OA of the outer support structure 304 in a region proximal the one or more weakened regions 310a, b and 312. Also, one or more of the weakened regions 310a, b and 312 may be disposed along a corner edge of the outer support structure 304 similar to the configuration illustrated in FIG. 19. In the illustrated embodiments of FIGS. 20 and 21, the weakened regions 310a, b and 312 are disposed along an outer perimeter of the outer support structure 304; however, some or all of the weakened regions 310a, b and 312 may be disposed along an inner perimeter, a top or bottom surface, or along a corner edge of the outer support structure 304.

Figure 22:
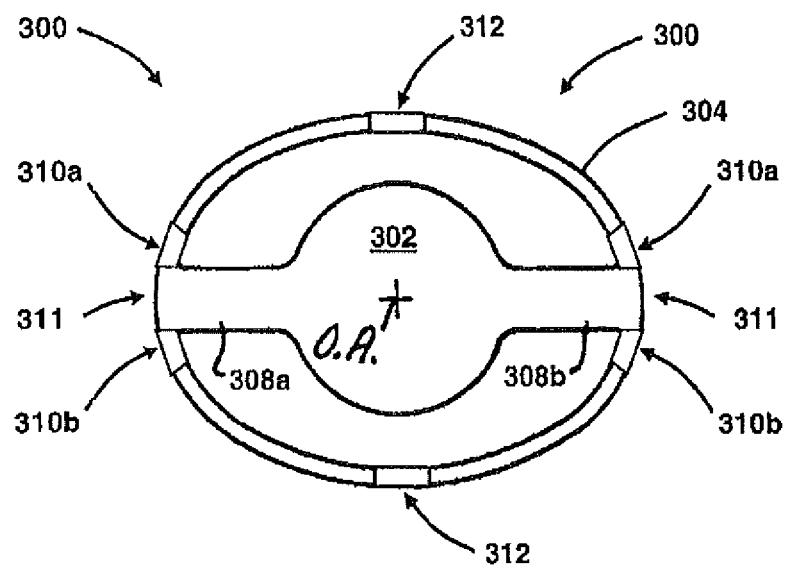
FIG. 22 is a plan view of an IOL having weakened portions made of a different material than other portion of the IOL.

Referring to FIG. 22, in certain embodiments, the outer support structure 304 is made of a first material and one or more of the weakened regions 310a, b and 312 are made of a second material that is more bendable than the first material. For example, the first material may be relatively stiff or hard (e.g., having a relatively high modulus of elasticity or tensile strength), while the second material is a relatively pliable or soft (e.g., having a relatively low modulus of elasticity or tensile strength). In certain embodiments, outer support structure 304 and one or more of the weakened regions 310a, b and 312 are made of the same material or substantially the same material, but the material in the one or more of the weakened regions 310a, b and 312 is processed in a different way from the material in the outer support structure 304. For example, the degree of polymerization may be different in the one or more of the weakened regions 310a, b and 312 than in the outer support structure 304. It will be understood that while the weakened regions 310a, b and 312 are shown as distinct regions in FIG. 22, these regions may be indistinguishable or essentially indistinguishable by visual inspection in an actual IOL. Also, the boundary between the weakened regions 310a, b and 312 and the outer support structure may be extended, gradual, or non-existent. For example, the boundary may be defined, in certain embodiments, by a gradual transition from the first material to the second material or by a gradual change in the degree of polymerization between the weakened regions 310a, b and 312 than in the outer support structure 304.

Any or all of the weakened regions 310a, b and 312 may be configured to form a hinge or to perform the function of a hinge, for example by extending about the optical axis OA by a relatively small circumferential distance, for example less than about 2 mm, preferably less than 1 mm, and more preferably less than 0.5 mm. Alternatively, any or all of the weakened regions 310a, b and 312 may be configured to form an elongated region in which the weakened regions 310a, b and/or 312 deform by varying amount along the region in response to the ciliary muscle 34 and/or the capsular bag 22. Such an elongate regions is preferably greater than about 2 mm and may be, for example, between about 2 mm to about 3 mm or between about 3 mm to about 5 mm or even greater than 5 mm.

Referring again to FIG. 20, for example, the intermediate weakened regions 312 may be circumferentially disposed equidistant or approximately equidistant between first and the second intermediate members 308a, b. In some embodiments, the outer support structure 304 comprises a first arm 314 and a second arm 318 separate and distinct from the first arm, the first arm 314 being connected or coupled to the first weakened region 308a located near the first intermediate region 308a and second arm 318 being connected or coupled to the first weakened region 308a located near the second intermediate region 308b.

Figure 23:
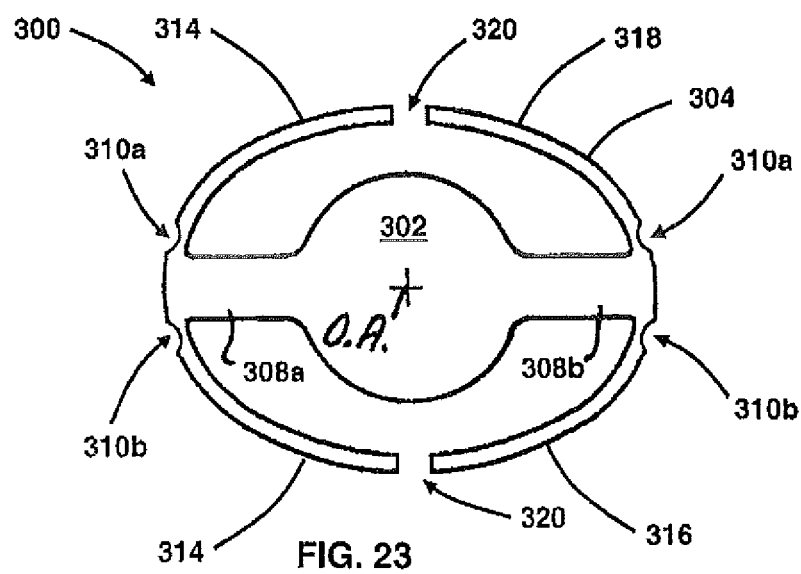
FIG. 23 is a plan view of an IOL having weakened portions and a void between arms of the IOL.
Figure 24:
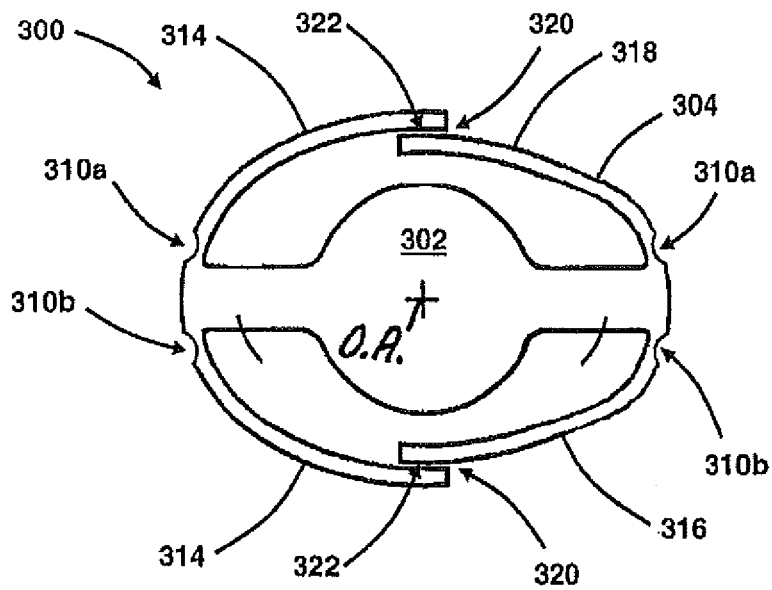
FIG. 24 is a plan view of another embodiment of an IOL having weakened portions and a void between arms of the IOL.

Referring to FIGS. 23 and 24, in certain embodiments, the first and second arms 314, 318 are separate and distinct and the IOL 300 further comprises a void 320 between the first arm 314 and the second arm 318. Such separation between the first and second arms 314, 318 may be useful in providing a predetermined performance of the outer support structure 304 and/or the first and second intermediate members 308a, b in response the ciliary muscle 34 and/or capsular bag 22. For example, referring to FIG. 23, the void 320 between the first and second arms 314, 318 may be configured so that the arms slide toward one another, but do not twist or buckle, as the outer support structure 304 is compressed in response to contraction of the ciliary muscle 34. In such embodiments the first and second arms 314, 318 may also rotate relative to the first and second intermediate members 308a, b. Preferably, the void is sufficiently large that the distal ends of the first and second arms 314, 318 adjacent the voids 320 do not touch when the outer support structure is in its most compressed configuration within the eye. As shown in FIG. 23, a distance between a first distal end of first arm 314 and a first distal end of second arm 318 is less than a diameter of the optic 302 along a major axis of the IOL 300. The optic 302 is positioned between the first distal end of the first arm 314 and a second distal end of the first arm 314 along a minor axis of the IOL 300, and is positioned between the first distal end of the second arm 318 and a second distal end of the second arm 318 along the minor axis of the IOL 300. A maximum width of the IOL 300 along the minor axis is greater than a maximum width of the optic 302 along the minor axis.

Referring to FIG. 24, at least a portion of the first arm 314 may be slidably disposed to at least a portion of the second arm 318. For example, the first and second arms 314, 318 may be configured to press against one another at their distal end and to slide as the capsular bag 22 changes shape during accommodation. Alternatively, the distal ends of the first and second arms 314, 318 may be kept in close contact with one another by using clamp or other appropriate device (not shown) for maintaining the distal end in contact with one another as the outer support structure is compressed and/or expanded during accommodation. In some embodiments, the first and second arms 314, 318 is configured so that the distal ends are in close proximity to one another, but are not necessarily or always in contact with one another as the outer support structure 304 is compress and/or expanded.

Figure 25:
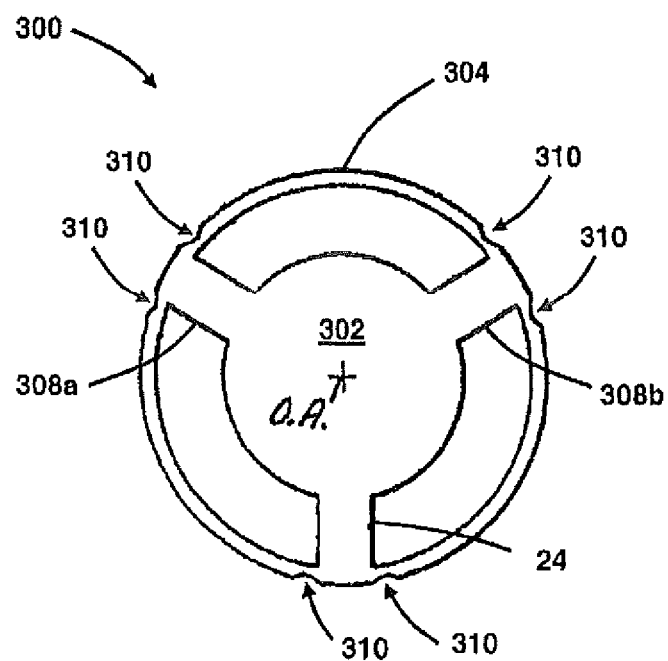
FIG. 25 is a plan view of an IOL having a circular outer support ring and weakened portions.

Referring to FIG. 25, the IOL 300 may comprise a third intermediate member 324 extending between and connecting the optic 302 and the outer support structure 304. Additionally or alternatively, the outer support member may be configured to be circular, as illustrated in FIG. 25, rather that oval shaped, as illustrated in FIGS. 20-24. In the illustrated embodiment shown in FIG. 25, the IOL 300 may further comprise the intermediate weakened regions 310 shown in FIGS. 20-22 (not shown). Also, the weakened regions 310a, b and/or 312 for the embodiment illustrated in FIG. 25 may have any of the structures or configurations discussed with regard to the embodiments discussed for FIGS. 20-24, where appropriate.

Referring again to FIG. 20, the intraocular lens 300 may comprise the optic 302 and the outer support structure 304, wherein the outer support structure 304 completely surrounds or encircles the optic 302 and the intermediate members 308. In such embodiments, the intermediate members 308 extend between and couple or connect the optic 302 and the outer support structure 304. Also, the outer support structure 304 comprises a first weakened region 310a disposed proximal the first intermediate member 308a and a second weakened region 310b disposed proximal the first intermediate member 308a. The first and second weakened regions 310a, b are configured to allow angular motion between the first intermediate member 308a and the outer support structure 304 in response to the ciliary muscle 34 of the eye.

The configuration, number and location of the weakened areas or portions or of the hinges in each of the illustrated embodiments are intended merely to be illustrative and, in practice, will depend on various factors such as the number and configuration of the intermediate members, the materials used, and the mode of deformation desired.

Furthermore, the outer support structures and outer rings and intermediate members in the IOLs of the embodiments in each of the FIGS. 1-25 are not intended to be limited to use with optics of any particular structure or type of material. For instance, the optics may be formed of rigid biocompatible materials such as polymethyl methacrylate (PMMA) or deformable materials such as silicone polymeric materials, acrylic polymeric materials, hydrogel polymeric materials, and the like. In addition, the optic bodies may be either refractive or diffractive.

In the most preferred embodiments, the optic body has a diameter in the range of about 3.5 to about 7 mm and, optimally, in the range of about 5 mm to about 6 mm. The overall diameter of the IOL, including the intermediate members and outer ring in unstressed conditions, is preferably about 8 mm to about 13 mm. Additionally, the optic has a far-vision correction power for infinity in an unaccommodated state.

A series of tests were run on a prototype IOL in order to evaluate the performance of the IOL under compression. The prototype IOL had the configuration of IOL 120' shown in FIG. 18A and was formed entirely of a unitary, reinforced cross-linked silicone polymeric material of the type described in Christ U.S. Pat. Nos. 5,236,970, 5,376,694, 5,494,946, 5,661,195, 5,869,549, and 6,277,147. The disclosures of each of these U.S. patents are incorporated in their entirety herein by reference.

During the tests, it was observed that, when the IOL 120' was compressed an amount in the range of about 0.3 mm to about 1 mm, the image quality in the far zone 132 improved slightly, while the image quality in the near zone (add power=2D), decreased slightly.

Figure 26:
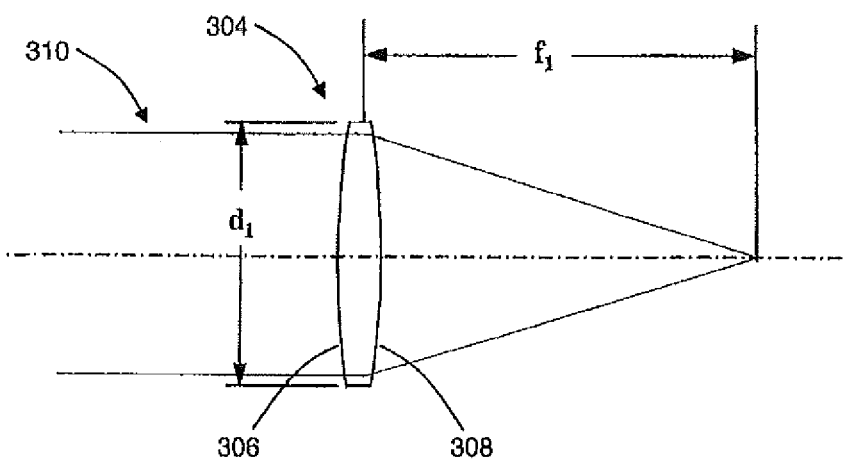
FIG. 26 is a side view of an optic from an IOL according to embodiments of the invention wherein the optic is not compressed.
Figure 27:
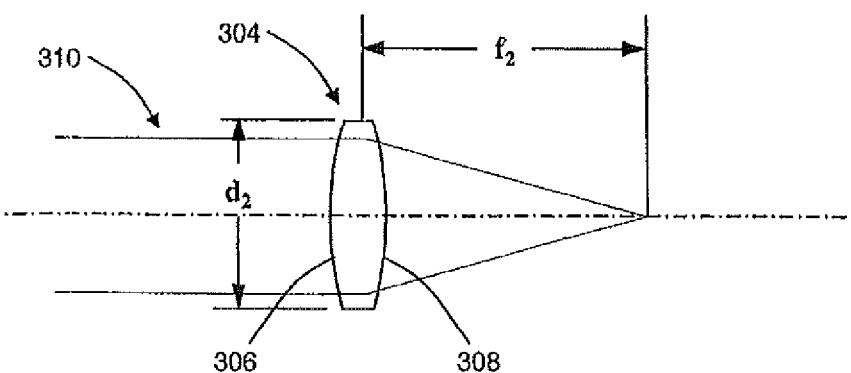
FIG. 27 is a side view of an optic from an IOL according to embodiments of the invention wherein the optic is compressed.

Referring to FIGS. 26 and 27, in certain embodiments, an equiconvex optic 304 comprises surfaces 306, 308. Those of skill in the art will recognize that the optic 304 may be characterized by a focal length f (e.g., $f_1$ in FIG. 26 and $f_2$ in FIG. 27) produced as light 310 is refracted by the surfaces 306, 308. It will also be recognized by those of skill in the art that the diopter power D of the equiconvex optic 304 is equal to 1/f, when f is in units of meters. For isotropic compression (e.g., $d_1$, $d_2$ in FIGS. 26 and 27, respectively) or deformation (e.g., deformation of the surfaces 306, 308 illustrated in FIGS. 26 and 27) of the equiconvex optic 304, there exists a relationship between the amount of diametric compression d (i.e. decrease in refractive zone size; for example $d_1 - d_2$) and the increase in diopter power (for example $D_2 - D_1$). With an increase in diopter power (e.g., from $D_1$ to $D_2$), at least some improvement in near vision can be expected. Referring again to FIG. 18A, by combining the increased diopter power obtained through deformation of the optic 126' with that obtained through axial movement, it is believed that enhanced accommodation can be achieved. In other words, a patient's presbyopia can be effectively reduced. Still better accommodation, or further reduction of presbyopia, can be obtained from the add power in the near zone 134 of a multifocal optic 126', or from the maximum add power of an aspheric optic.

Although the aforementioned tests were performed on an IOL 120' formed of a reinforced cross-linked silicone polymeric material, the principles of the invention will apply equally well to accommodating IOLs formed of any ophthalmically acceptable, deformable material or combination of materials. For instance, one or more of the optic 126', intermediate members 122', and outer ring 124' may be formed of an acrylic polymeric material. Particularly useful materials and combinations of materials are disclosed in U.S. patent application Ser. No. 10/314,069, filed Dec. 5, 2002.

Furthermore, while each of the accommodation assemblies illustrated herein comprises an outer ring surrounding and spaced from the optic with voids therebetween, and a plurality of intermediate members extending between and connecting the optic and the outer ring, these assemblies are merely exemplary. Other assembly configurations capable of effecting both axial movement and accommodating deformation of the optic are also included within the scope of the invention. For instance, accommodation and/or force transfer assemblies of the type shown in the aforementioned co-pending, commonly assigned U.S. patent application Ser. Nos. 09/656,661, 09/657,251, and 09/657,325, may also be suitable.

While the present invention has been described with respect to various specific examples and embodiments, it is to be understood that the invention is not limited thereto and that it can be variously practiced within the scope of the following claims.

What is claimed is:

1. An accommodating intraocular lens for implantation within a capsular bag of an eye, comprising:
   an optic having an outer periphery and centered about an optical axis;
   an outer support structure configured to be positioned within the capsular bag of the eye and having a first arcuate arm and a second arcuate arm disposed about the optic and along an outer periphery of the intraocular lens and spaced apart from the optic, the outer periphery of the intraocular lens having a generally oval shape with a major axis and a minor axis, the first arcuate arm having a first proximal end terminating in a first distal end and a second proximal end terminating in a second distal end, the second arcuate arm having a third proximal end terminating in a third distal end and a fourth proximal end terminating in a fourth distal end, the outer support structure including a first void located on the minor axis and between the first distal end of the first arcuate arm and the third distal end of the second arcuate arm such that the first distal end and the third distal end are not in contact with each other and a distance between the first distal end and the third distal end is less than a diameter of the optic along the major axis, the outer support structure including a second void diametrically opposed to the first void across the optic located on the minor axis between the second distal end of the first arcuate arm and the fourth distal end of the second arcuate arm such that the second distal end and the fourth distal end are not in contact with each other and a distance between the second distal end and the fourth distal end is less than a diameter of the optic along the major axis;
   a first plate-like intermediate member having a proximal end attached to the optic at a portion of the outer periphery of the optic that is positioned on the major axis, and a distal end attached to first and second proximal ends of the first arcuate arm; and
   a second plate-like intermediate member diametrically opposed to the first plate-like intermediate member, the second plate-like intermediate member having a proximal end attached to the optic at a portion of the outer periphery of the optic that is positioned on the major axis, and a distal end attached to third and fourth proximal ends of the second arcuate arm;
   wherein the optic is positioned between the first distal end of the first arcuate arm and the second distal end of the first arcuate arm along the minor axis, and the optic is positioned between the third distal end of the second arcuate arm and the fourth distal end of the second arcuate arm along the minor axis, and
   wherein the intraocular lens further comprises weakened regions disposed along the first arcuate arm and the second arcuate arm, the weakened regions positioned in proximity to the first and second proximal ends of the first arcuate arm and the third and fourth proximal ends of the second arcuate arm, and wherein the weakened regions are configured to provide for relative motion between the first and second distal ends of the first arcuate arm and the third and fourth distal ends of the second arcuate arm during accommodation.

2. The intraocular lens of claim 1, wherein the weakened regions are configured to provide for motion of the first arm and second arm relative to the optic during accommodation.

3. The intraocular lens of claim 2, wherein each of the weakened regions comprises a hinge.

4. The intraocular lens of claim 2, wherein each of the weakened regions has a radial thickness that is less than a radial thickness of the outer support structure in a region proximal to the weakened region.

5. The intraocular lens of claim 2, wherein each of the weakened regions has a thickness along the optical axis that is less than a thickness along the optical axis of the outer support structure in a region proximal to the weakened region.

6. The intraocular lens of claim 2, wherein the outer support structure is made of a first material and the weakened regions are made of a second material that is more bendable than the first material.

7. The intraocular lens of claim 2, wherein the weakened regions are circumferentially disposed between the distal end of the first intermediate member and the first arm.

8. The intraocular lens of claim 7, wherein the weakened regions have a radial thickness that is less than a radial thickness of the outer support structure in a region proximal to the weakened regions.

9. The intraocular lens of claim 1, wherein the first arm and the second arm are configured so that the first arm and the second arm move toward each other during accommodation such that the distance between the first distal end of the first arm and the first distal end of the second arm decreases.

10. The intraocular lens of claim 9, wherein the first void is sized such that the first distal end of the first arm and the first distal end of the second arm do not touch each other when the outer support structure is in its most compressed configuration within the eye, and the second void is sized such that the second distal end of the first arm and the second distal end of the second arm do not touch each other when the outer support structure is in its most compressed configuration within the eye.

11. The intraocular lens of claim 1, wherein a maximum width of the intraocular lens along the minor axis is greater than a maximum width of the optic along the minor axis.

* * * * *